(12) United States Patent
Longo et al.

(10) Patent No.: US 10,702,405 B2
(45) Date of Patent: Jul. 7, 2020

(54) INTRAVASCULAR IMPLANTS

(71) Applicant: Vesper Medical, Inc., Wayne, PA (US)

(72) Inventors: Michael A. Longo, Glenmoore, PA (US); Christopher N. Korkuch, Chester Springs, PA (US); William James Harrison, Signal Mtn, TN (US); Thea Rose Sander, Conshohocken, PA (US)

(73) Assignee: Vesper Medical, Inc., Wayne, PA (US)

( * ) Notice: Subject to any disclaimer, the term of this patent is extended or adjusted under 35 U.S.C. 154(b) by 0 days.

(21) Appl. No.: 15/852,192

(22) Filed: Dec. 22, 2017

(65) Prior Publication Data

US 2018/0116833 A1 May 3, 2018

Related U.S. Application Data

(62) Division of application No. 15/471,980, filed on Mar. 28, 2017.

(Continued)

(51) Int. Cl.
*A61F 2/89* (2013.01)
*A61F 2/915* (2013.01)
(Continued)

(52) U.S. Cl.
CPC .............. *A61F 2/89* (2013.01); *A61F 2/848* (2013.01); *A61F 2/915* (2013.01); *A61F 2/93* (2013.01); *A61F 2002/8483* (2013.01); *A61F 2002/91566* (2013.01); *A61F 2002/91575* (2013.01); *A61F 2210/0014* (2013.01); *A61F 2230/0008* (2013.01); *A61F 2230/0023* (2013.01);

(Continued)

(58) Field of Classification Search
CPC .. A61F 2/89; A61F 2/915; A61F 2002/91558; A61F 2250/0012; A61F 2250/0018; A61F 2250/0029
See application file for complete search history.

(56) References Cited

U.S. PATENT DOCUMENTS 5,397,355 A 3/1995 Marin et al.
5,449,373 A 9/1995 Pinchasik et al.
(Continued)

FOREIGN PATENT DOCUMENTS

EP 800801 10/1997
WO 2015038790 A1 3/2015
(Continued)

OTHER PUBLICATIONS

International Search Report and Written Opinion issued for International Application No. PCT/US2017/024614, dated May 31, 2017.

(Continued)

*Primary Examiner* — Christopher D. Prone
(74) *Attorney, Agent, or Firm* — Meunier Carlin & Curfman LLC

(57) ABSTRACT

A radially expandable, tubular stent, includes a first section having a first crush resistance force and a second section have a second crush resistance force, wherein the first crush resistance force is less than the second crush resistance force. The first section is connected to the second section to form a tube, connection of the first and second sections extending in an axial direction of the tube.

15 Claims, 20 Drawing Sheets

Related U.S. Application Data

(60) Provisional application No. 62/316,128, filed on Mar. 31, 2016.

(51) Int. Cl.
*A61F 2/848* (2013.01)
*A61F 2/93* (2013.01)

(52) U.S. Cl.
CPC .. *A61F 2230/0069* (2013.01); *A61F 2250/001* (2013.01); *A61F 2250/0015* (2013.01); *A61F 2250/0018* (2013.01); *A61F 2250/0029* (2013.01); *A61F 2250/0036* (2013.01); *A61F 2250/0037* (2013.01); *A61F 2250/0039* (2013.01); *A61F 2250/0098* (2013.01)

(56) References Cited

U.S. PATENT DOCUMENTS

| | | |
|---|---|---|
| 5,827,321 A | 10/1998 | Roubin et al. |
| 5,836,966 A | 11/1998 | St Germain |
| 5,843,120 A | 12/1998 | Israel et al. |
| 5,843,175 A | 12/1998 | Frantzen |
| 5,868,780 A | 2/1999 | Lashinski et al. |
| 5,868,782 A | 2/1999 | Frantzen |
| 5,911,754 A | 6/1999 | Kanesaka et al. |
| 5,922,005 A | 7/1999 | Richter et al. |
| 5,938,697 A | 8/1999 | Killion et al. |
| 5,964,798 A | 10/1999 | Imran |
| 5,972,018 A | 10/1999 | Israel et al. |
| 6,027,526 A | 2/2000 | Limon et al. |
| 6,033,433 A | 3/2000 | Her et al. |
| 6,042,606 A | 3/2000 | Frantzen |
| 6,059,811 A | 5/2000 | Pinchasik et al. |
| 6,068,656 A | 5/2000 | Von Oepen |
| 6,083,259 A | 7/2000 | Frantzen |
| 6,106,548 A | 8/2000 | Roubin et al. |
| 6,113,627 A | 9/2000 | Jang |
| 6,123,721 A | 9/2000 | Jang |
| 6,146,403 A | 11/2000 | St. Germain |
| 6,156,052 A | 12/2000 | Richter |
| 6,179,868 B1 | 1/2001 | Burpee et al. |
| 6,183,507 B1 | 2/2001 | Lashinski et al. |
| 6,190,403 B1 | 2/2001 | Fischell et al. |
| 6,200,334 B1 | 3/2001 | Jang |
| 6,203,569 B1 | 3/2001 | Wijay |
| 6,235,053 B1 | 5/2001 | Jang |
| 6,241,762 B1 | 6/2001 | Shanley |
| 6,261,319 B1 | 7/2001 | Kveen et al. |
| 6,287,336 B1 | 9/2001 | Globerman et al. |
| 6,299,635 B1 | 10/2001 | Frantzen |
| 6,309,414 B1 | 10/2001 | Rolando et al. |
| 6,325,821 B1 | 12/2001 | Gaschino et al. |
| 6,325,825 B1 | 12/2001 | Kula et al. |
| 6,402,777 B1 | 6/2002 | Globerman et al. |
| 6,428,570 B1 | 8/2002 | Globerman |
| 6,443,982 B1 | 9/2002 | Israel et al. |
| 6,451,049 B2 | 9/2002 | Vallana et al. |
| 6,461,380 B1 | 10/2002 | Cox |
| 6,461,381 B2 | 10/2002 | Israel et al. |
| 6,464,722 B2 | 10/2002 | Israel et al. |
| 6,475,236 B1 | 11/2002 | Roubin |
| 6,478,816 B1 | 11/2002 | Kveen et al. |
| 6,485,508 B1 | 11/2002 | McGuinness |
| 6,485,509 B2 | 12/2002 | Killion et al. |
| 6,497,723 B1 | 12/2002 | Starck et al. |
| 6,540,775 B1 | 4/2003 | Fischell et al. |
| 6,635,084 B2 | 10/2003 | Israel et al. |
| 6,638,300 B1 | 10/2003 | Frantzen |
| 6,641,609 B2 | 11/2003 | Globerman |
| 6,660,019 B1 | 12/2003 | Richter et al. |
| 6,679,911 B2 | 1/2004 | Burgermeister |
| 6,682,554 B2 | 1/2004 | Oepen et al. |
| 6,692,522 B1 | 2/2004 | Richter |
| 6,699,281 B2 | 3/2004 | Vallana et al. |
| 6,706,061 B1 | 3/2004 | Fischell et al. |
| 6,709,453 B2 | 3/2004 | Pinchasik et al. |
| 6,730,116 B1 | 5/2004 | Wolinsky et al. |
| 6,746,479 B2 | 6/2004 | Her et al. |
| 6,761,731 B2 | 7/2004 | Majercak |
| 6,764,506 B2 | 7/2004 | Roubin et al. |
| 6,786,922 B2 | 9/2004 | Schaeffer |
| 6,790,227 B2 | 9/2004 | Burgermeister |
| 6,818,015 B2 | 11/2004 | Hankh et al. |
| 6,923,829 B2 | 8/2005 | Boyle et al. |
| 6,939,373 B2 | 9/2005 | Gomez et al. |
| 6,945,993 B2 | 9/2005 | Kveen et al. |
| 7,004,968 B2 | 2/2006 | Lootz et al. |
| 7,029,493 B2 | 4/2006 | Majercak et al. |
| 7,037,330 B1 | 5/2006 | Rivelli, Jr. et al. |
| 7,060,088 B1 | 6/2006 | Fischell et al. |
| 7,060,090 B2 | 6/2006 | Thornton |
| 7,070,614 B1 | 7/2006 | Neuss et al. |
| 7,131,993 B2 | 11/2006 | Gregorich |
| 7,141,062 B1 | 11/2006 | Pinchasik et al. |
| 7,273,494 B2 | 9/2007 | Rolando et al. |
| 7,316,710 B1 | 1/2008 | Cheng et al. |
| 7,326,243 B2 | 2/2008 | Kveen et al. |
| 7,344,563 B2 | 3/2008 | Vallana et al. |
| 7,357,813 B2 | 4/2008 | Burgermeister |
| 7,402,169 B2 | 7/2008 | Killion |
| 7,431,732 B2 * | 10/2008 | Moriuchi ............... A61F 2/91 623/1.15 |
| 7,485,130 B2 | 2/2009 | St. Germain |
| 7,527,644 B2 | 5/2009 | Mangiardi et al. |
| 7,621,947 B2 | 11/2009 | Richter et al. |
| 7,648,526 B2 | 1/2010 | Sano et al. |
| 7,686,843 B2 | 3/2010 | Moore |
| 7,731,746 B2 | 6/2010 | Kveen et al. |
| 7,806,918 B2 | 10/2010 | Nissl et al. |
| 7,862,607 B2 | 1/2011 | McDermott et al. |
| 7,896,912 B2 | 3/2011 | Shanley |
| 8,012,196 B2 | 9/2011 | Smith et al. |
| 8,016,874 B2 | 9/2011 | Casey |
| 8,128,679 B2 | 3/2012 | Casey |
| 8,206,427 B1 | 6/2012 | Ryan et al. |
| 8,221,489 B2 | 7/2012 | Issenmann et al. |
| 8,257,424 B2 | 9/2012 | Orlowski |
| 8,267,991 B2 | 9/2012 | De Scheerder et al. |
| 8,317,854 B1 | 11/2012 | Ryan et al. |
| 8,317,859 B2 | 11/2012 | Snow et al. |
| 8,337,544 B2 | 12/2012 | Osman et al. |
| 8,348,990 B2 | 1/2013 | Boyle et al. |
| 8,470,021 B2 | 6/2013 | Magnuson et al. |
| 8,524,132 B2 | 9/2013 | Von Oepen et al. |
| 8,562,665 B2 | 10/2013 | Jang |
| 8,647,379 B2 | 2/2014 | McDermott et al. |
| 8,652,196 B2 | 2/2014 | Nissl |
| 8,668,731 B2 | 3/2014 | Kveen et al. |
| 8,888,837 B2 | 11/2014 | Obradović et al. |
| 8,974,514 B2 | 3/2015 | Anukhin et al. |
| 9,066,825 B2 | 6/2015 | Chanduszko |
| 9,320,627 B2 | 4/2016 | Casey |
| 9,375,810 B2 | 6/2016 | Mangiardi |
| 9,408,727 B2 | 8/2016 | Ainsworth et al. |
| 9,498,360 B2 | 11/2016 | Layman et al. |
| 9,554,927 B2 | 1/2017 | Bales, Jr. et al. |
| 9,561,123 B2 | 2/2017 | Bales, Jr. et al. |
| 9,622,850 B2 | 4/2017 | Bebb |
| 9,649,211 B2 | 5/2017 | Bonsignore et al. |
| 9,655,998 B2 | 5/2017 | Gemborys |
| 9,668,895 B2 | 6/2017 | Dreher |
| 9,668,898 B2 | 6/2017 | Wong |
| 9,693,860 B2 | 7/2017 | Sandstrom et al. |
| 9,700,448 B2 | 7/2017 | Snow et al. |
| 9,707,110 B2 | 7/2017 | McDermott et al. |
| 9,724,220 B2 | 8/2017 | Rasmussen |
| 9,770,348 B2 | 9/2017 | Wack |
| 9,795,496 B2 | 10/2017 | Armstrong et al. |
| 9,839,538 B2 | 12/2017 | Grewe et al. |
| 9,839,540 B2 | 12/2017 | Armstrong et al. |
| 2001/0014822 A1 | 8/2001 | Milo |
| 2001/0047200 A1 | 11/2001 | White et al. |
| 2002/0013616 A1 | 1/2002 | Carter et al. |

(56) References Cited

U.S. PATENT DOCUMENTS

| | | |
|---|---|---|
| 2002/0042648 A1 | 4/2002 | Schaldach et al. |
| 2002/0058990 A1 | 5/2002 | Jang |
| 2003/0009214 A1 | 1/2003 | Shanley |
| 2003/0014102 A1 | 1/2003 | Hong et al. |
| 2003/0100941 A1 | 5/2003 | Fischell et al. |
| 2003/0105513 A1 | 6/2003 | Moriuchi et al. |
| 2003/0105517 A1 | 6/2003 | White et al. |
| 2004/0054398 A1 | 3/2004 | Cully et al. |
| 2004/0054400 A1 | 3/2004 | Granada |
| 2004/0102835 A1 | 5/2004 | Israel et al. |
| 2004/0133265 A1 | 7/2004 | Duffy |
| 2004/0243216 A1* | 12/2004 | Gregorich ............... A61F 2/91 623/1.15 |
| 2004/0254627 A1 | 12/2004 | Thompson et al. |
| 2004/0267350 A1 | 12/2004 | Roubin et al. |
| 2005/0004657 A1 | 1/2005 | Burgermeister |
| 2005/0021130 A1 | 1/2005 | Kveen et al. |
| 2005/0060024 A1 | 3/2005 | Lee et al. |
| 2005/0080479 A1 | 4/2005 | Feng et al. |
| 2005/0125051 A1 | 6/2005 | Eidenschink et al. |
| 2006/0025852 A1 | 2/2006 | Armstrong et al. |
| 2006/0129227 A1 | 6/2006 | Hengelmolen |
| 2006/0173531 A1 | 6/2006 | Richter |
| 2007/0010869 A1 | 1/2007 | Sano |
| 2007/0213806 A1 | 9/2007 | Roubin et al. |
| 2007/0213807 A1 | 9/2007 | Roubin et al. |
| 2007/0219613 A1 | 9/2007 | Kao et al. |
| 2008/0009938 A1 | 1/2008 | Huang et al. |
| 2008/0051878 A1 | 2/2008 | Cheng et al. |
| 2008/0140181 A1 | 6/2008 | Reynolds et al. |
| 2008/0288048 A1 | 11/2008 | Rolando et al. |
| 2009/0018641 A1 | 1/2009 | Binkert |
| 2009/0062899 A1 | 3/2009 | Dang et al. |
| 2010/0004736 A1 | 1/2010 | Rolando et al. |
| 2010/0222864 A1 | 9/2010 | Rivelli, Jr. et al. |
| 2010/0241216 A1 | 9/2010 | Rolando et al. |
| 2011/0125251 A1 | 2/2011 | Cottone et al. |
| 2011/0106237 A1 | 5/2011 | Bonsignore et al. |
| 2011/0230957 A1 | 9/2011 | Bonsignore et al. |
| 2012/0043703 A1 | 2/2012 | Von Oepen et al. |
| 2012/0046729 A1 | 2/2012 | Von Oepen et al. |
| 2012/0046730 A1 | 2/2012 | Von Oepen et al. |
| 2012/0046731 A1 | 2/2012 | Von Oepen et al. |
| 2012/0046733 A1 | 2/2012 | Von Oepen et al. |
| 2012/0046739 A1 | 2/2012 | Von Oepen et al. |
| 2012/0143312 A1 | 6/2012 | Brown |
| 2012/0277844 A1 | 11/2012 | Wu |
| 2012/0310327 A1 | 12/2012 | McHugo |
| 2013/0178928 A1 | 7/2013 | Vyas et al. |
| 2013/0304192 A1 | 11/2013 | Chanduszko |
| 2013/0325141 A1 | 12/2013 | Gill et al. |
| 2014/0277365 A1 | 9/2014 | Gillespie |
| 2014/0277378 A1 | 9/2014 | Lane et al. |
| 2015/0105852 A1 | 4/2015 | Noffke et al. |
| 2015/0209167 A1 | 7/2015 | Mangiardi |
| 2015/0250580 A1 | 9/2015 | Besselink |
| 2016/0235562 A1 | 8/2016 | Casey |
| 2016/0250052 A1 | 9/2016 | Kaspar |
| 2016/0287418 A1 | 10/2016 | Cheng et al. |
| 2016/0310268 A1 | 10/2016 | Oba et al. |
| 2017/0035548 A1 | 2/2017 | Bebb et al. |
| 2017/0071768 A1 | 3/2017 | Krieger et al. |
| 2017/0086994 A1 | 3/2017 | Bales et al. |
| 2017/0100267 A1 | 4/2017 | Bales et al. |
| 2017/0224878 A1 | 8/2017 | Gemborys |
| 2017/0265998 A1 | 9/2017 | Sandstrom et al. |
| 2017/0312104 A1 | 11/2017 | McDermott et al. |
| 2017/0312105 A1 | 11/2017 | McDermott et al. |
| 2017/0340464 A1 | 11/2017 | Kovach et al. |

FOREIGN PATENT DOCUMENTS

| | | |
|---|---|---|
| WO | 2016046413 | 3/2016 |
| WO | 2017042329 | 3/2017 |
| WO | 2017050710 | 3/2017 |

OTHER PUBLICATIONS

International Preliminary Report on Patentability issued by the International Bureau in Application No. PCT/US2017/024614, dated Oct. 2, 2018.

\* cited by examiner

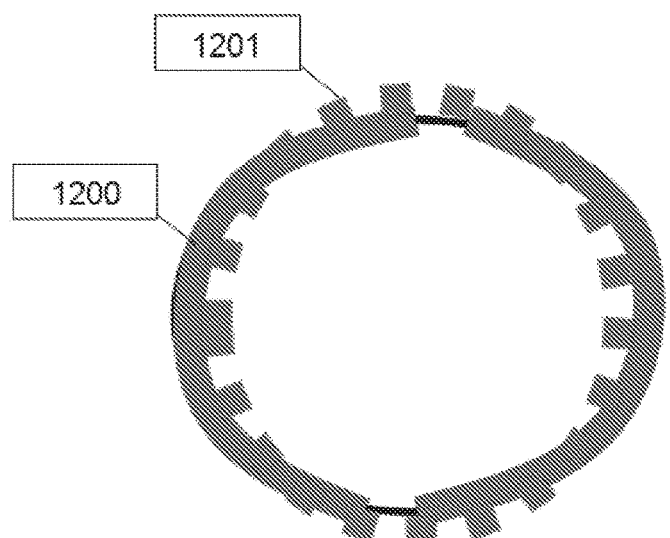
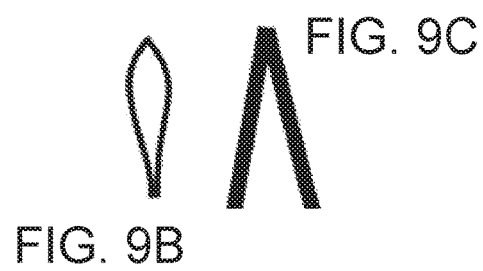
FIG. 9A  FIG. 9B  FIG. 9C
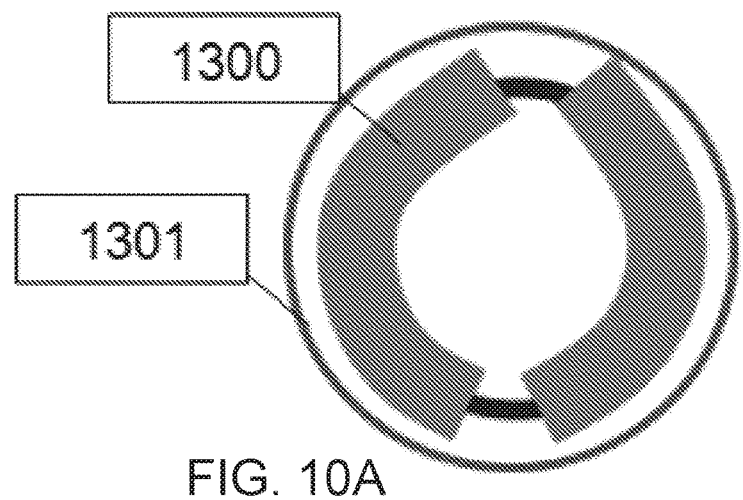
FIG. 10A  FIG. 10B  FIG. 10C

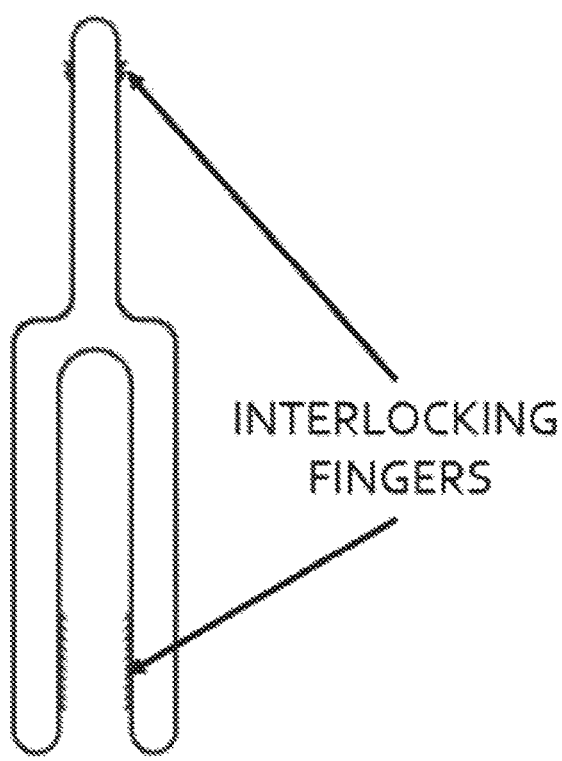
FIG. 20A
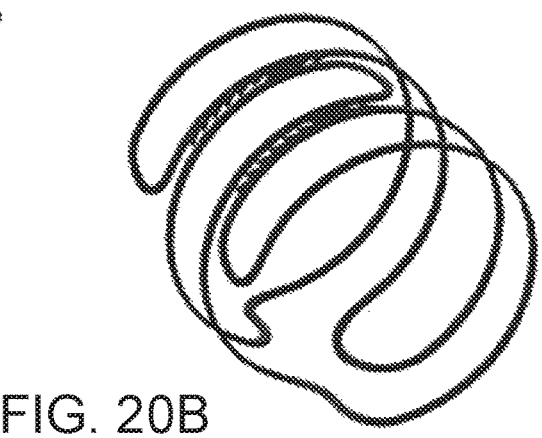
FIG. 20B
TUBE VIEW
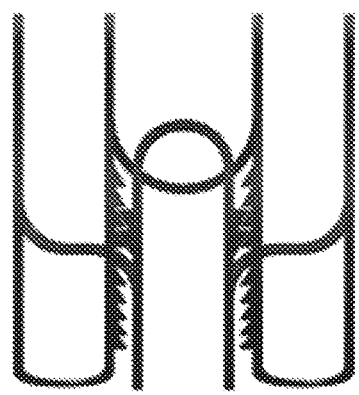 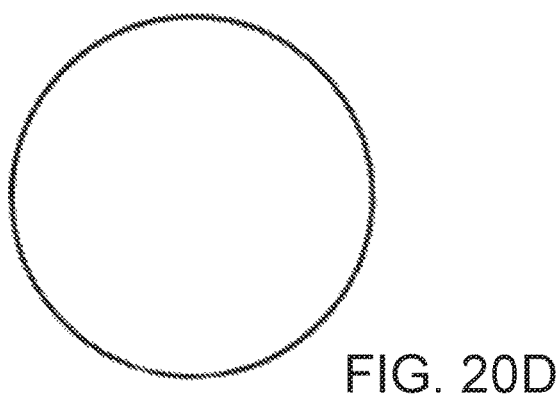
FIG. 20C   FRONT AND SIDE VIEW   FIG. 20D Diameter 2

Diameter 1
(no finger engagement)

CONFIG 1

CONFIG 4

CONFIG 2

CONFIG 5

CONFIG 3

CONFIG 6

INTRAVASCULAR IMPLANTS

CROSS REFERENCE TO RELATED APPLICATIONS

This application is a divisional of U.S. patent application Ser. No. 15/471,980, filed Mar. 28, 2017, which is a nonprovisional application of, and claims the priority benefit of, Provisional Application Ser. No. 62/316,128, filed Mar. 31, 2016, each of which is hereby incorporated by reference in its entirety for all purposes as if fully set forth herein.

BACKGROUND

Field of the Invention

Disclosed herein are stents for implantation within the body and methods for delivery and/or deployment. Certain embodiments disclosed herein may be used in procedures to treat May-Thurner syndrome and/or deep venous thrombosis and the resulting post-thrombotic syndrome.

Description of the Related Art

May-Thurner syndrome, also known as iliac vein compression syndrome, is a condition in which compression of the common venous outflow tract of the left lower extremity may cause various adverse effects, including, but not limited to, discomfort, swelling, pain, and/or deep venous thrombosis (DVT) (commonly known as blood clots). May-Thurner syndrome occurs when the left common iliac vein is compressed by the overlying right common iliac artery, leading to stasis of blood, which may cause the formation of blood clots in some individuals. Other, less common, variations of May-Thurner syndrome have been described, such as compression of the right common iliac vein by the right common iliac artery.

While May-Thurner syndrome is thought to represent between two to five percent of lower-extremity venous disorders, it frequently goes unrecognized. Nevertheless, it is generally accepted that May-Thurner syndrome is about three times more common in women than it is in men and typically manifests itself between the age of twenty and forty. Patients exhibiting both hypercoaguability and left lower extremity thrombosis may be suffering from May-Thurner syndrome. To confirm that diagnosis, it may be necessary to rule out other causes for hypercoagulable state, for example by evaluating levels of antithrombin, protein C, protein S, factor V Leiden, and prothrombin G20210A.

By contrast to the right common iliac vein, which ascends almost vertically parallel to the inferior vena cava, the left common iliac vein takes a more transverse course. Along this course, it lies under the right common iliac artery, which may compress it against the lumbar spine. Iliac vein compression is a frequent anatomic variant—it is thought that as much as 50% luminal compression of the left iliac vein occurs in a quarter of healthy individuals. However, compression of the left common iliac vein becomes clinically significant only if such compression causes appreciable hemodynamic changes in venous flow or venous pressure, or if it leads to acute or chronic deep venous thrombosis, which will be discussed in more detail below. In addition to the other problems associated with compression, the vein may also develop intraluminal fibrous spurs from the effects of the chronic pulsatile compressive force from the overlying artery.

The narrowed, turbulent channel associated with May-Thurner syndrome may predispose the afflicted patient to thrombosis. And, the compromised blood flow often causes collateral blood vessels to form—most often horizontal transpelvis collaterals, connecting both internal iliac veins to create additional outflow possibilities through the right common iliac vein. Sometimes vertical collaterals are formed, most often paralumbar, which can cause neurological symptoms, like tingling and numbness.

Current best practices for the treatment and/or management of May-Thurner syndrome is proportional to the severity of the clinical presentation. Leg swelling and pain is best evaluated by vascular specialists, such as vascular surgeons, interventional cardiologists, and interventional radiologists, who both diagnose and treat arterial and venous diseases to ensure that the cause of the extremity pain is evaluated. Diagnosis of May-Thurner syndrome is generally confirmed one or more imaging modalities that may include magnetic resonance venography, and venogram, which, because the collapsed/flattened left common iliac may not be visible or noticed using conventional venography, are usually confirmed with intravascular ultrasound. To prevent prolonged swelling or pain as downstream consequences of the left common iliac hemostasis, blood flow out of the leg should be improved/increased. Early-stage or uncomplicated cases may be managed simply with compression stockings. Late-stage or severe May-Thurner syndrome may require thrombolysis if there is a recent onset of thrombosis, followed by angioplasty and stenting of the iliac vein after confirming the diagnosis with a venogram or an intravascular ultrasound. A stent may be used to support the area from further compression following angioplasty. However, currently available stenting options suffer from several complications—including severe foreshortening, lack of flexibility (which can force the vessel to straighten excessively), vessel wear and eventual performation, increased load on and deformation of the stent causing early fatigue failure, and/or impedence of flow in the overlying left iliac artery potentially causing peripheral arterial disease. The compressed, narrowed outflow channel present in May-Thurner syndrome may cause stasis of the blood, which an important contributing factor to deep vein thrombosis.

Some patients suffering from May-Thurner syndrome may exhibit thrombosis while others may not. Nevertheless, those patients that do not experience thrombotic symptoms may still experience thrombosis at any time. If a patient has extensive thrombosis, pharmacologic and/or mechanical (i.e., pharmacomechanical) thrombectomy may be necessary. The hemostasis caused by May-Thurner syndrome has been positively linked to an increased incidence of deep vein thrombosis ("DVT").

Deep vein thrombosis, or deep venous thrombosis, is the formation of a blood clot (thrombus) within a deep vein, predominantly in the legs. The right and left common iliac are common locations for deep vein thrombosis, but other locations of occurrence are common. Non-specific symptoms associated with the condition may include pain, swelling, redness, warmness, and engorged superficial veins. Pulmonary embolism, a potentially life-threatening complication of deep vein thrombosis, is caused by the detachment of a partial or complete thrombus that travels to the lungs. Post-thrombotic syndrome, another long-term complication associated with deep venous thrombosis, is a medical condition caused by a reduction in the return of venous blood to the heart and can include the symptoms of chronic leg pain, swelling, redness, and ulcers or sores.

Deep vein thrombosis formation typically begins inside the valves of the calf veins, where the blood is relatively oxygen deprived, which activates certain biochemical pathways. Several medical conditions increase the risk for deep vein thrombosis, including cancer, trauma, and antiphospholipid syndrome. Other risk factors include older age, surgery, immobilization (e.g., as experienced with bed rest, orthopedic casts, and sitting on long flights), combined oral contraceptives, pregnancy, the postnatal period, and genetic factors. Those genetic factors include deficiencies with antithrombin, protein C, and protein S, the mutation of Factor V Leiden, and the property of having a non-O blood type. The rate of new cases of deep vein thrombosis increases dramatically from childhood to old age; in adulthood, about 1 in 1000 adults develops the condition annually.

Common symptoms of deep vein thrombosis include pain or tenderness, swelling, warmth, redness or discoloration, and distention of surface veins, although about half of those with the condition have no symptoms. Signs and symptoms alone are not sufficiently sensitive or specific to make a diagnosis, but when considered in conjunction with known risk factors can help determine the likelihood of deep vein thrombosis. Deep vein thrombosis is frequently ruled out as a diagnosis after patient evaluation: the suspected symptoms are more often due to other, unrelated causes, such as cellulitis, Baker's cyst, musculoskeletal injury, or lymphedema. Other differential diagnoses include hematoma, tumors, venous or arterial aneurysms, and connective tissue disorders.

Anticoagulation, which prevents further coagulation but does not act directly on existing clots, is the standard treatment for deep vein thrombosis. Other, potentially adjunct, therapies/treatments may include compression stockings, selective movement and/or stretching, inferior vena cava filters, thrombolysis, and thrombectomy.

BRIEF SUMMARY OF THE INVENTION

Accordingly, the present invention is directed to an intravascular stent that obviates one or more of the problems due to limitations and disadvantages of the related art.

An advantage of the present invention is to provide a radially expandable, tubular stent, including a first section having a first crush resistance force and a second section have a second crush resistance force, wherein the first crush resistance force is less than the second crush resistance force; and the first section connected to the second section to form a tube, connection of the first and second sections extending in an axial direction of the tube.

In another aspect of the present invention, further embodiment of a radially expandable, tubular stent, includes a plurality of circumferentially adjacent closed cells defining at least two axially repeating rings; and a plurality of linkage struts connecting respective ones of the circumferentially adjacent closed cells, wherein the plurality of linkage struts is fewer than the plurality of linkage struts such that fewer than the plurality of circumferentially adjacent closed cells in adjacent rings are connected by a linkage strut.

Further embodiments, features, and advantages of the intravascular stent, as well as the structure and operation of the various embodiments of the intravascular stent, are described in detail below with reference to the accompanying drawings.

It is to be understood that both the foregoing general description and the following detailed description are exemplary and explanatory only, and are not restrictive of the invention as claimed.

BRIEF DESCRIPTION OF THE DRAWINGS

The accompanying figures, which are incorporated herein and form part of the specification, illustrate an intravascular stent. Together with the description, the figures further serve to explain the principles of the intravascular stent described herein and thereby enable a person skilled in the pertinent art to make and use the intravascular stent.

FIG. 4A shows the stent uncompressed and unconstrained; FIG. 4B shows the stent highly compressed for delivery; and FIG. 4C shows the stent deployed within a blood vessel.

FIG. 9A shows the stent of FIG. 5B in comparison to a minimum reference vessel diameter.

FIGS. 9B-9C show the stronger struts and the weaker struts of the stent of FIG. 8A when the stent is at the minimum reference vessel diameter.

FIG. 10A shows the stent of FIG. 5B held within the lumen of a delivery device.

FIGS. 10B-10C show the stronger struts and the weaker struts of the stent of FIG. 8A when the stent held within the lumen of a delivery device.

FIGS. 20A-20H show various views of an implant having an expanded implantation size that may be selectively adjustable across a range of diameters.

DETAILED DESCRIPTION

Figure 1:
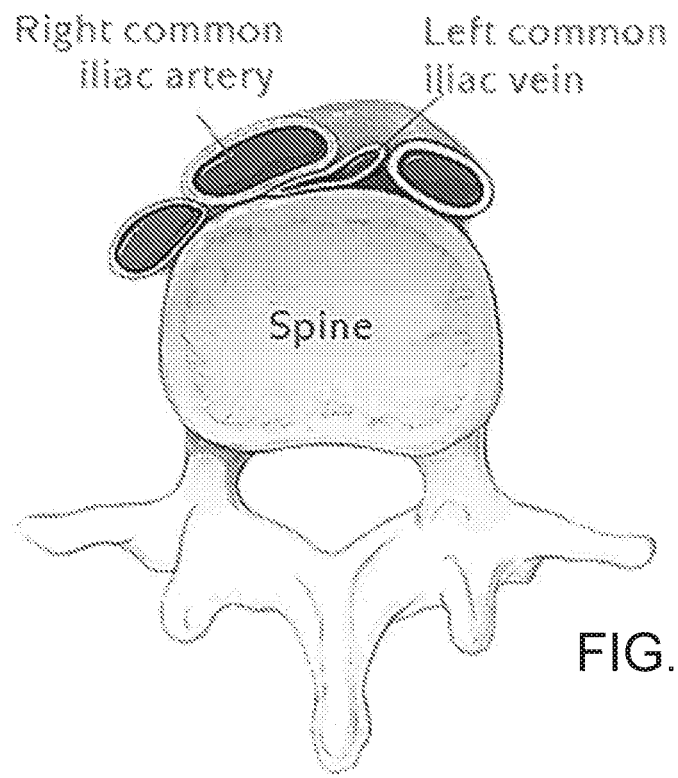
FIG. 1 shows an inferior-posterior view of the L5 lumbar and the bifurcations of the abdominal aorta and inferior vena cava.

May-Thurner syndrome, or iliac vein compression syndrome, occurs in the peripheral venous system when the iliac artery compresses the iliac vein against the spine as shown in FIG. 1. FIG. 1 illustrates a vertebra, the right and left common iliac arteries near the bifurcation of the abdominal aorta, and the right and left common iliac arteries near the bifurcation of the inferior vena cava. The bifurcations generally occur near the L5 lumbar vertebra. Thus, it can be seen that FIG. 1 shows an inferior-posterior view of the L5 lumbar and the bifurcations of the abdominal aorta and inferior vena cava.

As shown, the strong right common iliac artery has compressed the iliac vein causing it to become narrowed. This is one possible, if not a classic, manifestation of May-Thurner syndrome. Over time, such narrowing may cause vascular scarring which can result in intraluminal changes that could precipitate iliofemoral venous outflow obstruction and/or deep vein thrombosis. As discussed above, venous insufficiency (i.e., a condition in which the flow of blood through the veins is impaired) can ultimately lead to various deleterious pathologies including, but not limited to, pain, swelling, edema, skin changes, and ulcerations. Venous insufficiency is typically brought on by venous hypertension that develops as a result of persistent venous obstruction and incompetent (or subcompetent) venous valves. Current treatments for venous outflow obstruction include anticoagulation, thrombolysis, balloon angioplasty and stenting.

Figure 2:
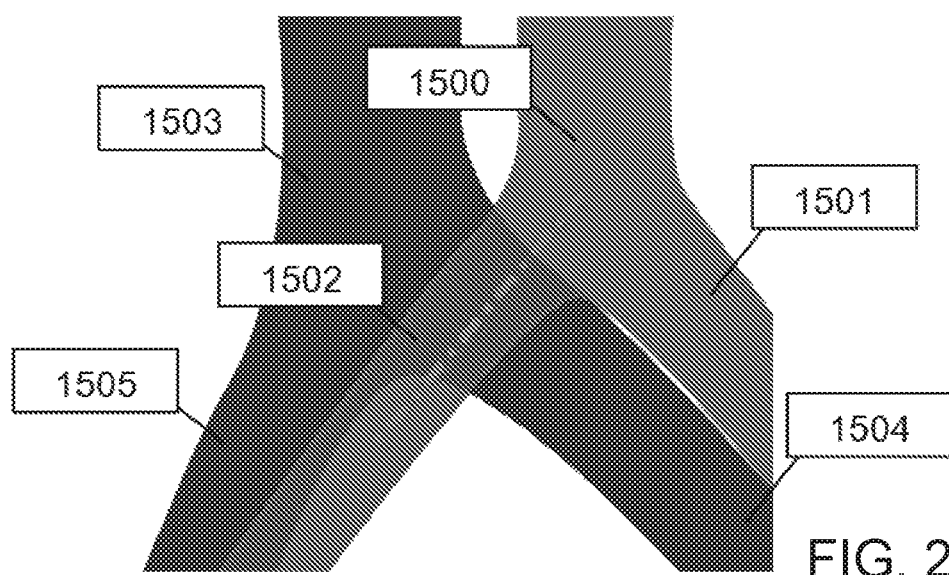
FIG. 2 shows a schematic of the standard overlap of the right common iliac artery over the left common iliac vein.

FIG. 2 illustrates the standard overlap of the right common iliac artery over the left common iliac vein. The arteries shown include the abdominal aorta 1500 branching into the left common iliac artery 1501 and the right common iliac artery 1502. The veins shown include the inferior vena cava 1503 branching into the left common iliac vein 1504 and right common iliac vein 1505. It will be understood that the rough diagram illustrated in FIG. 2 represents the view looking down on a patient laying face-up (i.e., an anterior-poster view of the patient at the location of the bifurcation of the abdominal aorta 1500 and the inferior vena cava 1503). The overlap of the right common iliac artery 1502, which is relatively strong and muscular, over the left common iliac vein 1504 can cause May-Thurner syndrome by pressing down on the vein 1504, crushing it against the spine, restricting flow, and, eventually, causing thrombosis and potentially partially or completely clotting off of the left common iliac vein 1054 and everything upstream of it (i.e., the venous system in the left leg, among others).

Figure 3:
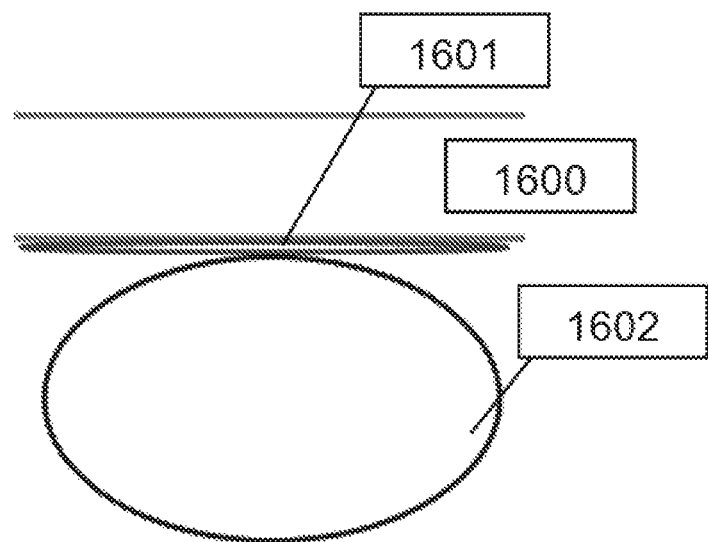
FIG. 3 shows a cross-sectional schematic of the arteriovenous system shown in FIG. 2 taken along the gray dotted line.

FIG. 3 illustrates a cross-section of the arterio-venous system shown in FIG. 2 taken along the gray dotted line.

Shown in schematic are the right common iliac artery 1600, the left common iliac vein 1601, and a vertebra 1602 of the spine (possibly the L5 lumbar vertebra of the lumbar spine). As can be seen, the right common iliac artery 1600 is substantially cylindrical, due to its strong, muscular construction (among other potential factors). That strong, muscular artery has pressed down on the left common iliac vein 1601, until it has almost completely lost patency, i.e., it is nearly completely pinched off. It will be understood that May-Thurner syndrome may indeed involve such severe pinching/crushing of the underlying left common iliac vein 1601 against the vertebra 1602 of the lumbar spine. However, it will also be understood that May-Thurner syndrome may involve much less pinching/crushing of the underlying left common iliac vein 1601 against the vertebra 1602. Indeed, embodiments disclosed herein are appropriate for the treatment of various degrees of May-Thurner syndrome, including full crushing/pinching of the left common iliac vein 1602 by the right common iliac artery 1600. Other embodiments disclosed herein are appropriate for the treatment of various degrees of May-Thurner syndrome, including, but not limited to a crush/pinch of the underlying left common iliac vein 1601 of between about 10-95%, about 15-90%, about 20-85%, about 25-80%, about 30-75%, about 35-70%, about 40-65%, about 45-60%, and about 50-55%, or any other crush/pinch that could merit treatment using one or more of the devices disclosed herein.

Figure 4A:
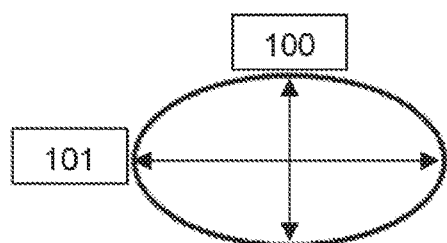
FIGS. 4A-4C show an embodiment of an elliptical stent in three different states.
Figure 4B:
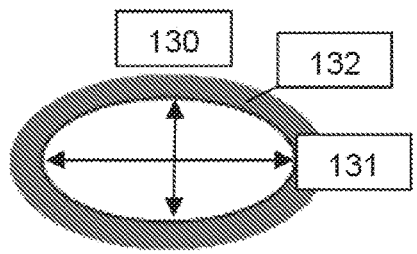
Figure 4C:
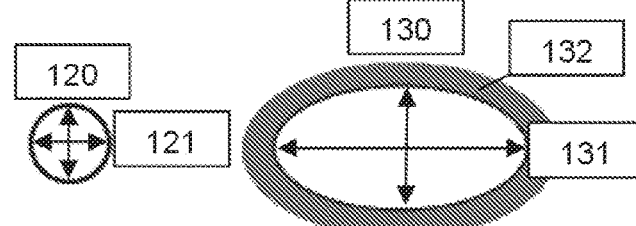

In some embodiments, a self-expanding elliptical stent is provided, including elliptical stents having a high crush resistance, but a low radial force on the vessel wall. Therefore, some embodiments of stents discussed herein, including elliptical stents, may be useful in the treatment of May-Thurner syndrome. FIGS. 4A-4C illustrate an embodiment of an elliptical stent in various states: FIG. 4A shows the stent uncompressed and unconstrained (e.g., sitting on a table); FIG. 4B shows the stent comparatively highly compressed for delivery within a patient and constrained by a delivery device (e.g., a catheter-base delivery device); finally, FIG. 4C shows the stent compressed and constrained by and within the left common iliac vein of a patient.

More specifically, FIG. 4A shows one embodiment of an elliptical stent in a first state (e.g., an uncompressed, unconstrained state) having an unconstrained cross-section with a first cross-sectional diameter 100 (or diameter across a minor axis of an ellipse) in a first direction and a second cross-sectional diameter 101 (or diameter across a major axis of an ellipse) in a second direction (perpendicular to the first direction). As can be seen, when uncompressed, the first cross-sectional diameter 100 may be less than the perpendicular, second cross-sectional diameter thereby defining a substantially elliptical cross-section.

FIG. 4B illustrates the elliptical stent of FIG. 4A in a second state (e.g., a highly compressed state) having a crimped cross-sectional with a first cross-sectional diameter 120 in the first direction and a second cross-sectional diameter 121 in the perpendicular, second direction. As can be seen, when compressed for delivery, the elliptical stent may have a first cross-sectional diameter that is substantially equal to its perpendicular, second cross-sectional diameter—that is to say that when in the second, highly compressed, or delivery, state, the elliptical stent may have a cross sectional profile that is substantially circular.

FIG. 4C illustrates the elliptical stent of FIGS. 4A-4B in a third state (e.g., an implanted or deployed state) and deployed or placed within a blood vessel (e.g., a left common iliac vein). As shown in FIG. 4C, the stent may be placed within a vessel 132 and thereby be constrained or restricted by the intraluminal wall of the vessel 132. As will be easily understood, when deployed, the stent pushes outward to hold open the vessel 132 to maintain patency. FIG. 4C shows that after deployment, at least some embodiments of the elliptical stents disclosed herein main maintain their elliptical cross-section to hold open the vessel 132 in an elliptical cross-sectional shape, rather than in a standard circular cross-sectional shape—that is to say that after deployment, the first cross-sectional diameter 130 (or diameter across a minor axis of an ellipse) in the first direction is less than the second cross-sectional diameter 131 (or diameter across a major axis of an ellipse) in the perpendicular second direction.

In some embodiments, the first cross-sectional diameter 100 when in the unconstrained first state is greater than the first cross-sectional diameter 130 when in the deployed third state, which is greater than the first cross-sectional diameter 120 when in the highly compressed second state. Stated more simply, the elliptical stent has a larger cross-sectional diameter when uncompressed than when deployed in the lumen of a vessel. This is natural as the stent must be under some compression when deployed to be of any use holding the vessel open. And, the stent has a smaller cross-sectional diameter when compressed into a delivery device than when uncompressed (e.g., on a table) or deployed in a vessel lumen. The stent must be able to traverse tortuous blood vessel systems to arrive at its deployment location—and it must be smaller than the lumens through which it must pass, so as to not scrape and damage the vessel walls.

As just discussed, some of the stents disclosed herein have an elliptical cross section (i.e., a first diameter across a minor axis smaller than a second, perpendicular diameter across a major axis). In some embodiments of the elliptical (or other) stents disclosed herein, the stent generates a first radial force in the first cross-sectional direction (e.g., FIG. 4A 100) that is substantially equal to a second radial force in the second cross-section direction (e.g., FIG. 4A 101). In other embodiments of the elliptical (or other) stents disclosed herein, the stent is advantageously capable of generating a first radial force in the first cross-sectional direction (e.g., FIG. 4A 100) and a different, lesser second radial force in the perpendicular second cross-sectional direction (e.g., FIG. 4A 101). In still other embodiments of the elliptical (or other) stents disclosed herein, the stent generates a first racial force in the first cross-sectional direction (e.g., FIG. 4A 100) and a different, greater second radial force in the perpendicular second cross-sectional direction (e.g., FIG. 4A 101).

Some embodiments of the stents disclosed herein may have one or more strong sections in the wall of the stent and one or more weak sections in the wall of the stent. By selectively positioning these strong and weak sections, the stent may be tailored to have selective crush-resistance. Various examples, which are not intended to be exhaustive, of such selective crush-resistance are discussed below.

Figure 5A:
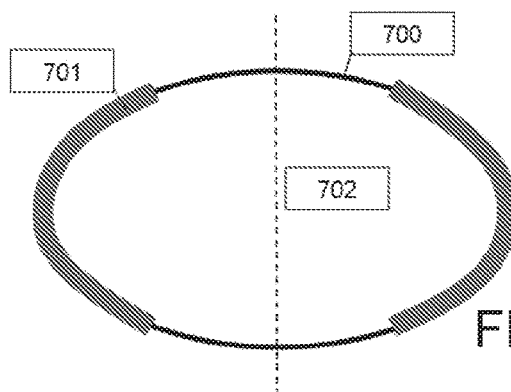
FIG. 5A is an embodiment of an elliptical stent having bilaterally symmetrical weaker sections and bilaterally symmetrical stronger sections.

FIG. 5A illustrates an embodiment of an elliptical stent having bilaterally symmetrical weaker sections of the stent wall (e.g., struts or other structures) and bilaterally symmetrical stronger sections of the stent wall (e.g., struts or other structures). The stent may have an elliptical cross-sectional shape (although it should be understood that it may have other cross-sectional shapes, when uncompressed, highly compressed, or deployed) in its uncompressed state that is symmetrical across its center axis 702 (e.g., FIG. 4A 100) that is substantially perpendicular to the stent's longitudinal axis (which is generally the same as the longitudinal axis of the blood vessel into which the stent is deployed, when deployed). As shown in FIG. 5A, the stent has two stronger sections 701 (e.g., reinforced sections, load bearing sections, etc.) that are separated by two weaker sections 700 (e.g., connection portions). The strong sections 701 are shown as being symmetric across the center axis 701 of the ellipse such that the stronger sections 701 are positioned in the more convex portions of the ellipse. Such a configuration of strong sections 701 and weak sections 700 may create a higher resistance to crush force in the vertical cross-sectional direction than the horizontal cross-sectional direction. And, the weak sections 700 may create a point where the stent is more susceptible to collapse along the center axis 701 than the points working away from the axis.

Figure 5B:
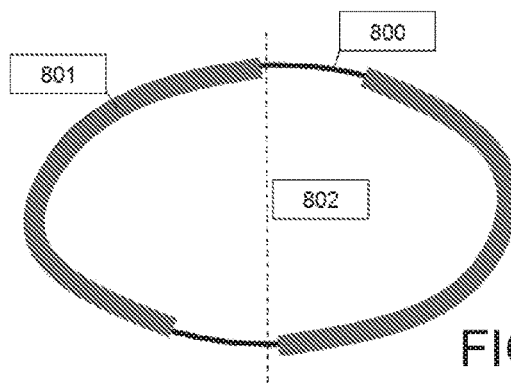
FIG. 5B is an embodiment of an elliptical stent having bilaterally asymmetrical weaker sections and bilaterally asymmetrical stronger sections.

FIG. 5B illustrates an embodiment of an elliptical stent having bilaterally asymmetrical weaker sections of the stent wall (e.g., struts or other structures) and bilaterally asymmetrical stronger sections of the stent wall (e.g., struts or other structures). The stent may have an elliptical cross-sectional shape (although it should be understood that it may have other cross-sectional shapes, when uncompressed, highly compressed, or deployed) in its uncompressed state that is symmetrical across its center axis 802 (e.g., the same as FIG. 4A 100) that is substantially perpendicular to the stent's longitudinal axis (which is generally the same as the longitudinal axis of the blood vessel into which the stent is deployed, when deployed). Similar to the stent shown in FIG. 5A, the stent shown in FIG. 5B has two stronger sections 801 (e.g., reinforced sections, load bearing sections, etc.) that are separated by two weaker sections 800 (e.g., connection portions). However, unlike the stent shown in FIG. 5A, the stent shown in FIG. 5B is not symmetric around the center axis 802 of the ellipse. This configuration of stronger sections 801 and weaker sections 800 may create a higher resistance to crush force in the vertical cross-sectional direction than in the horizontal cross-sectional direction while minimizing the vertical weakness of the weaker sections 800.

Figure 6A:
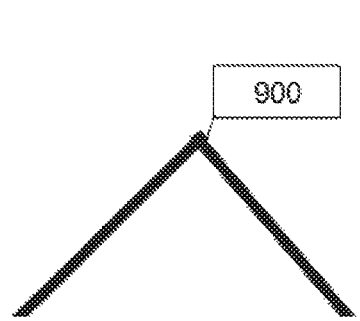
FIGS. 6A-6B show an embodiment of the struts of the weaker sections of the stents of FIGS. 5A-5B.
Figure 6B:
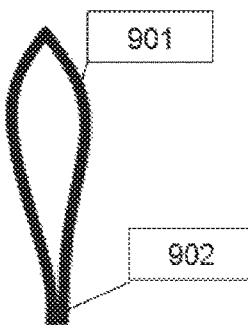

FIGS. 6A-6B illustrate an embodiment of the struts of the weaker sections 700, 800 of the stents shown in FIGS. 5A-5B. The struts of the weaker sections may comprise a first strut that has a first strut state 900 of FIG. 6A and a second strut state 901 of FIG. 6B. The shape change of the stent cross-section is discussed further below and references the changes in strut state to enable/facilitate changes in stent shape. The first strut state 900 of FIG. 6A is partially collapsed. By contrast, the second strut state 901 of FIG. 6B is fully collapsed. The strut may collapse through an increase in loading. The base of the strut comes into contact 902 when fully collapsed—such contact at the base of the strut may prevent further collapse upon additionally increased loading. The deformation from partially collapsed to fully collapsed may be reversible deformation. The weak sections discussed above (i.e., weaker sections 700, 800) are created through a series of at least one first strut(s).

Figure 7A:
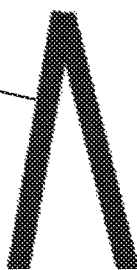
FIGS. 7A-7B show an embodiment of the struts of the stronger sections of the stents of FIGS. 5A-5B.
Figure 7B:
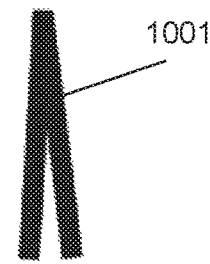

FIGS. 7A-7B illustrate an embodiment of the struts of the stronger sections 701, 801 of the stents shown in FIGS. 5A-5B. The struts of the stronger sections may comprise a first strut that has a first strut state 1000 of FIG. 7A and a second strut state 1001 of FIG. 7B. The first strut state 1000 of FIG. 7A is partially collapsed. By contrast, the second strut state 1001 of FIG. 7B is more collapsed. The strut may collapse through an increase in loading, just like the weaker struts of FIGS. 6A-6B—however, collapse of the stronger sections (e.g., shown in FIGS. 7A-7B) requires more force than the collapse of the weaker sections (e.g., shown in FIGS. 6A-6B). The shape change of the stent cross-section is discussed further below and references the changes in strut state to enable/facilitate changes in stent shape. The first strut state 1000 of FIG. 7A is shown substantially unconstrained with little to no collapse. By contrast, the second strut state 1001 of FIG. 7B is shown partially collapsed, but not completely collapsed. The strut may collapse through an increase in loading. The deformation from partially collapsed to fully collapsed may be reversible deformation. The strong section discussed above (i.e., stronger sections 701, 801) are created through a series of at least one second strut(s).

The discussion surrounding FIGS. 6A-6B and FIGS. 7A-7B involves, among other things, creating weaker struts and stronger struts merely using less material and more material, respectively. While that simple solution can prove quite effective, it will be understood that many other ways of creating weaker sections and stronger section exist. For example, strut density (i.e., number of struts in a given space) may be increased for the stronger sections while strut density may be decreased for the weaker sections. Alternatively, strut angles (or lack thereof) and prismatic configuration may be used to increase or decrease section strength. Any method or way of creating a stent having sections of varying strength may be used.

Figure 8A:
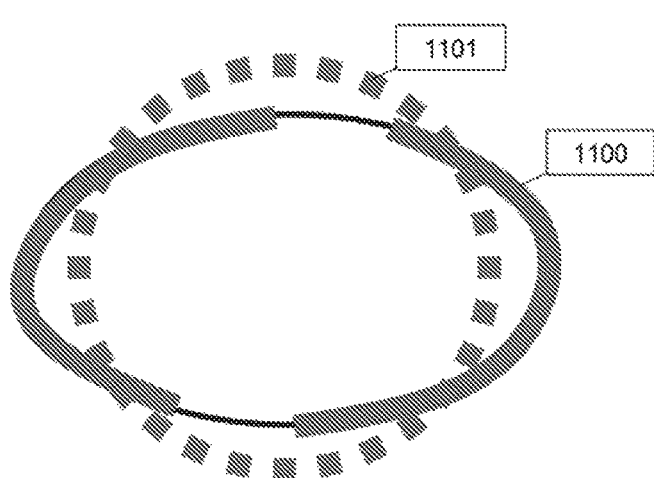
FIG. 8A shows the stent of FIG. 5B in comparison to a maximum reference vessel diameter.
Figure 8B:
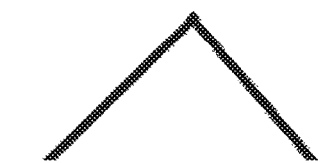
FIGS. 8B-8C show the stronger struts and the weaker struts of the stent of FIG. 8A when the stent is at the maximum reference vessel diameter.
Figure 8C:

FIG. 8A illustrates a cross-section of the stent of FIG. 5B in comparison to a maximum reference vessel diameter 1100. The diameter of the reference vessel 1101 creates a generally deformable circumference which contains and must compress (at least to some extent) the stent. In this case, the circumference of the stent is just less than the circumference of the maximum vessel diameter. As can be seen, the stent 1100 has stronger sections (shown in FIG. 8C) that remain relatively uncompressed and weaker sections (shown in FIG. 8B) that remain relatively uncompressed. That is to say (with reference to the descriptions of FIGS. 6A-6B and 7A-7B, both the stronger struts and the weaker struts are in their first strut state when the stent 1100 is in this maximum vessel diameter configuration. The maximum (circular) diameter of a blood vessel which can be treated using the devices (e.g., stents, vascular devices, vascular endoprostheses) disclosed herein is about 10-23 mm, about 12-22 mm, about 14-21 mm, about 16-20 mm, about 17-19 mm, and about 18 mm.

FIG. 9A illustrates a cross-section of the stent 1200 of FIG. 5B in comparison to a minimum reference vessel diameter 1201. The diameter of the reference vessel 1201 creates a generally deformable circumference which contains and must compress (to some extent) the stent. Again, the circumference of the stent is just less than the circumference of the maximum vessel diameter. However, it can be easily seen that the stent 1200 of FIG. 9A is more compressed than the stent 1100 of FIG. 8A. The change in circumference of the stent from the maximum reference vessel to the minimum reference vessel is achieved substantially through the transition of the weaker struts from the first strut state to the second strut state of the first, weaker struts (though it should be understood that some deformation of the stronger struts may be possible). Indeed, Due to the stronger structure of the stronger struts (second strut), the stronger struts stay mostly in their first strut state, although some minor collapse may occur. As can be seen, the stent 1100 has stronger sections (shown in FIG. 9C) that remain relatively uncompressed and weaker sections (shown in FIG. 9B) that compress almost completely. That is to say (with reference to the descriptions of FIGS. 6A-6B and 7A-7B, the stronger struts remain substantially in their first strut state and the weaker struts collapse substantially to their second strut state when the stent 1100 is in this minimum vessel diameter configuration. The result achieved using this dual-strength or multi-strength (as more than one strength region may be used) is the sizing at a maximum and minimum reference diameter with minimal radial force (e.g., resistance of the weak section). The higher radial force of the stronger section is present to resist crush of the vessel, but does not impart high radial force onto the vessel. Therefore, the stent at its minimum vessel sizing may be significantly circular. The minimum (circular) diameter of a blood vessel which can be treated using the devices (e.g., stents, vascular devices, vascular endoprostheses) disclosed herein is about 7-20 mm, about 8-18 mm, about 9-16 mm, about 10-14 mm, about 11-13 mm and about 12 mm.

FIG. 10A illustrates the stent 1300 of FIG. 5B held within and compressed by a delivery device, e.g., the wall a delivery catheter 1301. The transition from the minimum vessel diameter to the crimped diameter (e.g., highly compressed diameter, delivery diameter, etc.) is achieved through the transition of the stronger struts from the first strut state to the second strut state. The weaker struts compress first and therefore can merely stay in the second strut state. FIGS. 10B and 10C illustrate the weaker struts and the stronger struts, respectively, compressed down to their second strut state. The outer diameter of a delivery catheter in which stents, vascular devices, and vascular endoprostheses as disclosed herein may be delivered can be in the range of about 7-12 Fr, about 8-11 Fr, about 9-10 Fr, or any other diameter that can both hold the device and fit through the target vasculature.

Figure 11A:
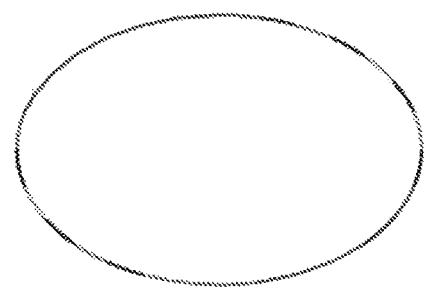
FIGS. 11A-11E are various views of an embodiment of an elliptical stent having stronger sections and weaker sections.
Figure 11B:
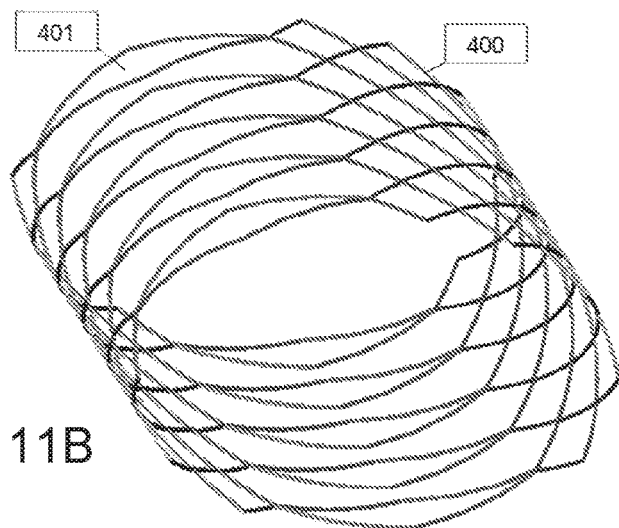
Figure 11C:
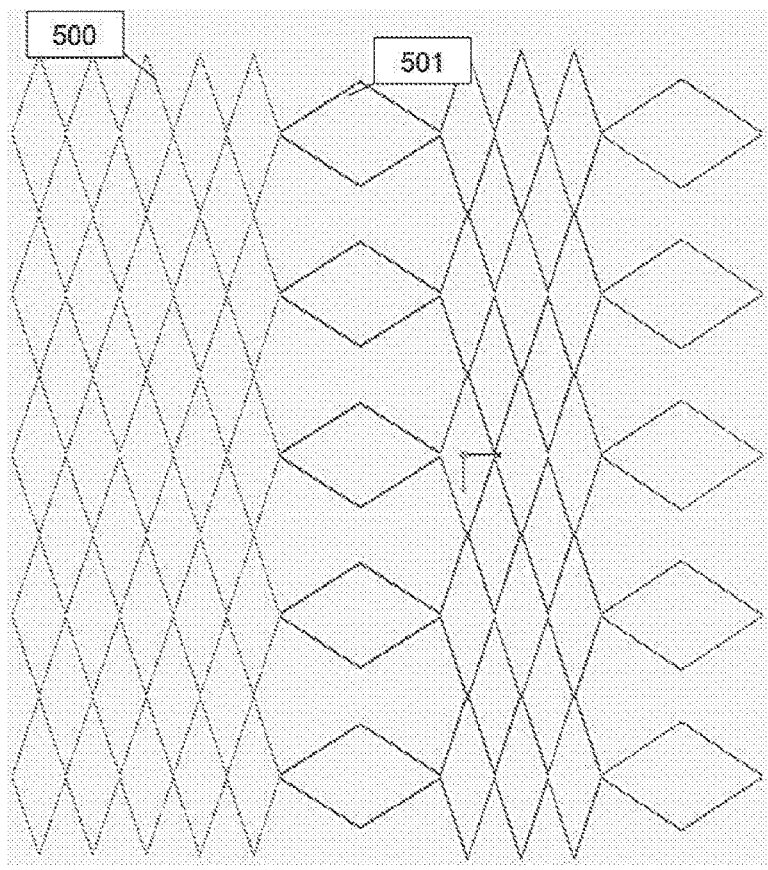
Figure 11D:
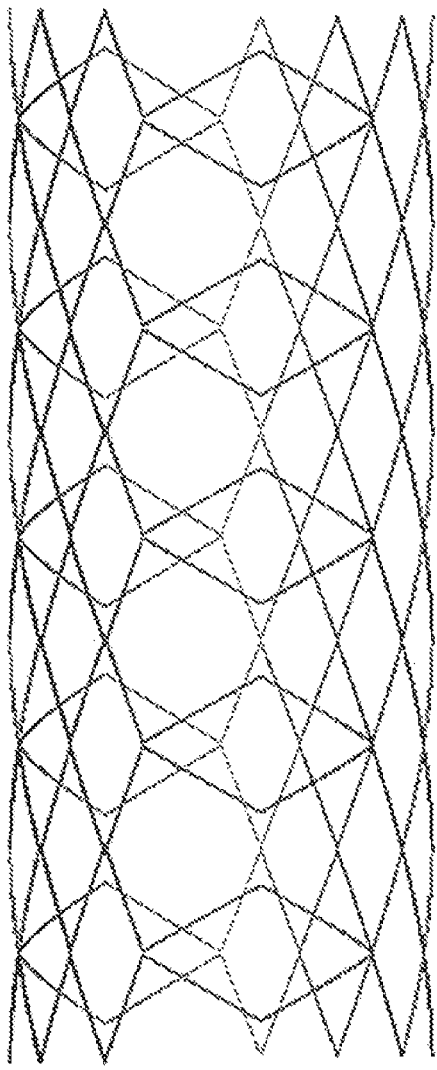
Figure 11E:
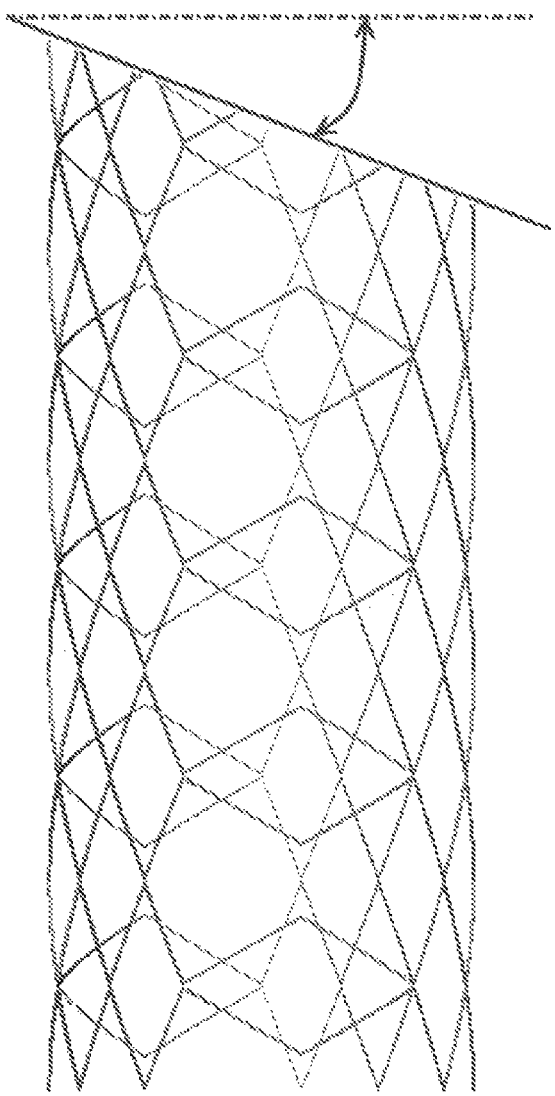

FIGS. 11A-11E illustrate various views of an embodiment of an elliptical stent having stronger sections and weaker sections, as discussed above. FIG. 11A simply illustrates a top/front view of an embodiment of an elliptical stent, showing an elliptical shape. FIG. 11B illustrates a three-quarter view of an embodiment of an elliptical stent. FIG. 11 shows that the weak section may comprise only a single first strut 401 whereas the stronger section may comprise a series of second struts 400. The single first strut 401 may be stronger than each second strut of the series of second struts. Alternatively, the single first strut 401 may be weaker than each second strut of the series of second struts. But, regardless of their individual strength, in this embodiment, the weaker section has less resistance to deformation than does the stronger section. FIG. 11C illustrates a flat pattern view (not necessarily in scale) of an embodiment of an elliptical stent. The stronger section is made up of several second struts 500 and the weaker section is made up of a single first struts 501 in a vertically repeating pattern. As shown, the stronger section and the weaker sections do not need to each contain the same number of repeating struts. In at least some embodiments, the weak sections are configured so as to not make contact with each other when in an unconstrained state and in a fully compressed state. FIG. 11D illustrates a side view of view of an embodiment of an elliptical stent. FIG. 11E illustrates an embodiment of an elliptical stent similar to that shown in FIG. 11D, except that it includes an angled distal end. This angled distal end may be configured to match the vessel geometry where the left common iliac vein and the right common iliac vein merge into the inferior vena cava. In such a configuration, the end of the stent having the angled termination may be deployed so as to reside at the merger of the two iliac veins (i.e., the bifurcation of the inferior vena cava) while the length of the stent extends distally or downward into the left common iliac vein. This may advantageously serve to provide additional support to the vein(s) at the vena caval bifurcation. Of course, the stent may have any angle necessary to match a given patient's anatomy. But, the angle will generally be in the range of about 5-45°, about 10-40°, about 15-35°, about 20-30°, or about 25°, or any other angle necessary to fit a patient's vasculature.

Figure 12:
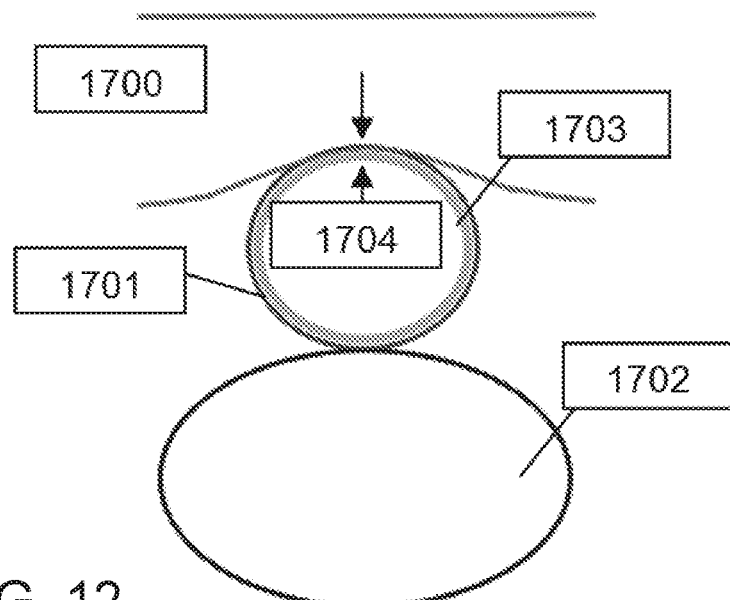
FIG. 12 shows the anatomical cross section of FIG. 3 with a circular stent deployed in the left common iliac vein.

FIG. 12 illustrates the same anatomical cross section shown in FIG. 3 with the addition of a circular stent 1703 deployed in the left common iliac vein 1701. To achieve full fill (e.g., full apposition of the exterior surface of the stent against the intraluminal wall) of the vein, the circular stent must exert significant force, denoted by arrows 1704, on the right common iliac artery 1700. Levels of force high enough to achieve clinically meaningful fill of the vein (e.g., substantially full or meaningful apposition of the exterior surface of the stent against the intraluminal wall) may result in several adverse effects, including, but not limited to, vessel wear and eventual perforation, increased load on and deformation of the stent causing early fatigue failure, and/or impedance of blood flow in the right common iliac artery 1700, which may result in peripheral arterial disease. Note, the vertebra 1702 of the spine does not displace and is assumed substantially rigid with little-to-no give.

Figure 13:
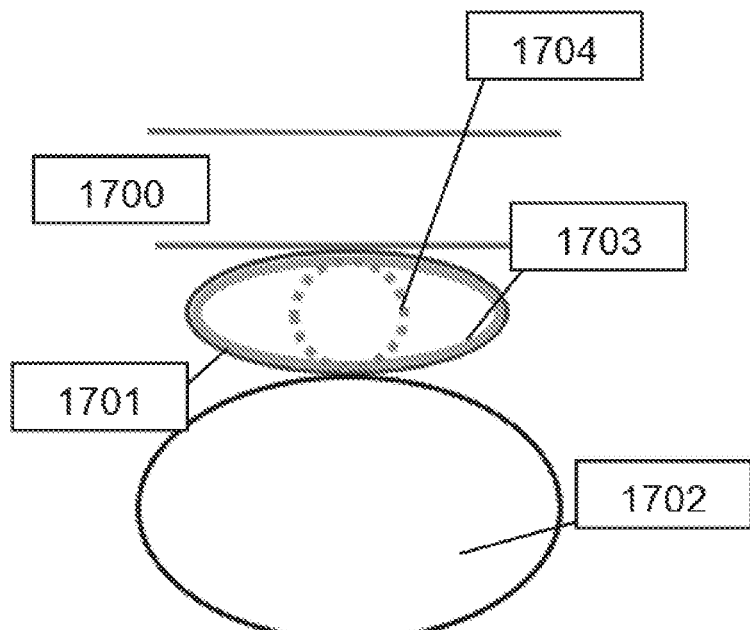
FIG. 13 shows the anatomical cross section of FIG. 3 with an elliptical stent deployed in the left common iliac vein.

FIG. 13 illustrates the same anatomical cross section shown in FIG. 3 with the addition of an elliptical stent 1703 deployed in the left common iliac vein. It should be noted that the elliptical stent 1703 of FIG. 13 has the same circumference as the circular stent 1704 of FIG. 12. Use of elliptical stents 1703 may advantageously allow in the creation of patency in the left common iliac vein 1701 without much of the added load cause by the increased height of a circular stent 1703. Using an elliptical stent may advantageously allow a comparatively low vertical load. To achieve the same low vertical load using a circular stent, a significantly smaller stent would be used. And, such a smaller stent would have a dramatically lower cross-sectional area than the elliptical stent. Reduced load minimizes the likelihood of the complication referenced above with respect to circular stents for the treatment of May-Thurner syndrome (e.g., in the description of FIG. 12), while still providing a similar cross-sectional area to maintain flow and prevent clotting off of the vein. In some embodiments, specific orientation of the pre-loaded or crimped elliptical implant in a delivery catheter is mitigated as certain implant designs disclosed herein may allow for some level of self-alignment. The elliptical stent can be capable of self-orientation in a compressed vein: the high radial force vs. low radial force of the elliptical design could cause the implant to rotate/orient itself such that the higher radial force/crush resistance section (long axis) is perpendicular to the compression force. Due to the constraints on the left common iliac vein 1701 from the right common iliac artery 1700 and the L5 lumbar vertebra 1702, the elliptical stent can be deployed at an angle up to but not including 90 degrees from horizontal and self-align back to horizontal.

Figure 14:
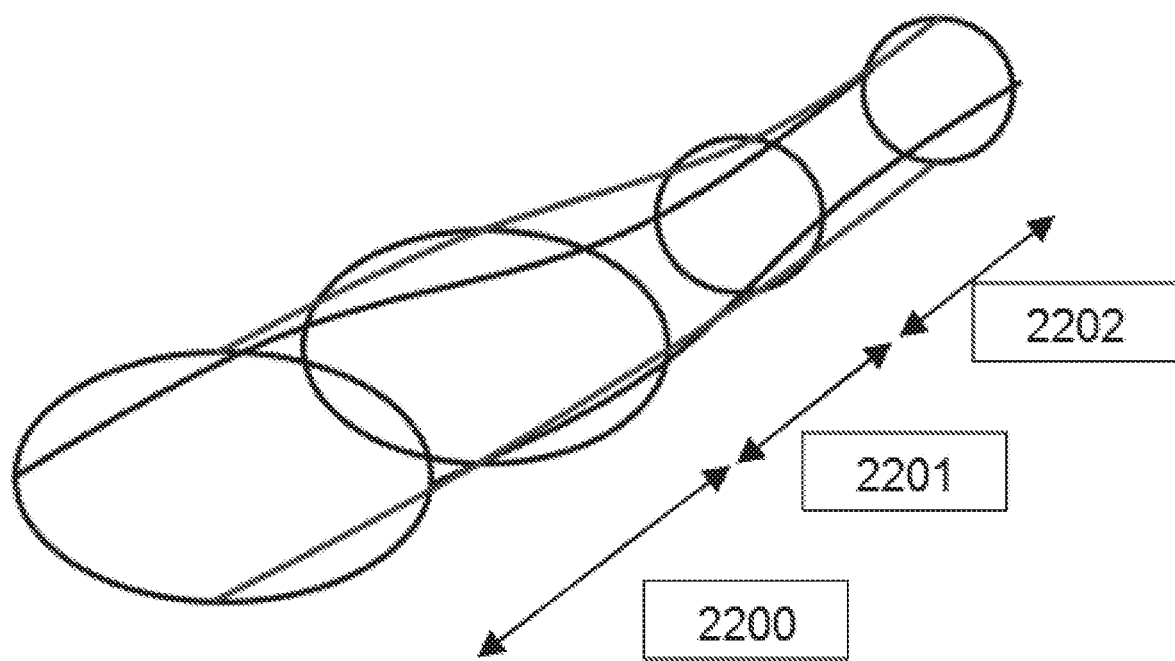
FIG. 14 is a hybrid stent having a first section, a second section, and a third transitional section.

In some embodiments, a hybrid stent including at least a first section comprising an elliptical stent portion and at least a second section comprising another, different stent portion, is provided. FIG. 14 illustrates a schematic view of a hybrid stent having a first section 2200 a second section 2202 and a third transitional section 2201, which transitions from the first section to the second section. In some embodiments, the first section 2200 of the hybrid stent is an elliptical stent such as disclosed elsewhere herein. In some embodiments, the second section 2202 comprises a portion of a stent having high radial force circular stent with flexible axial length. In other embodiments, the second section 2202 may comprises any other type of stent, including those disclosed herein. In some embodiments, the third section 2201 gently or gradually transitions from the stent of the first section 2200 to the stent of the second section 2202 so as to conform best to the patient's vasculature. Such hybrid stents may advantageously prove useful in the simultaneous treatment of May-Thurner syndrome and an accompanying deep venous thrombosis, such as deep venous thrombosis in the iliac and common femoral vein.

Figure 14A:
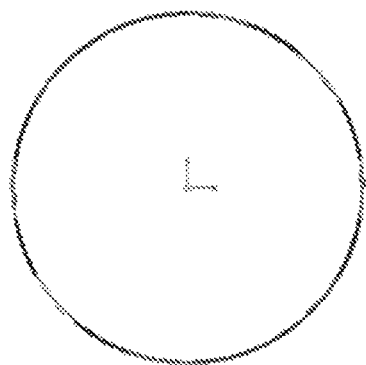
FIGS. 14A-14C show various views of an embodiment of a stent having both high radial force and flexibility along its length.
Figure 14B:
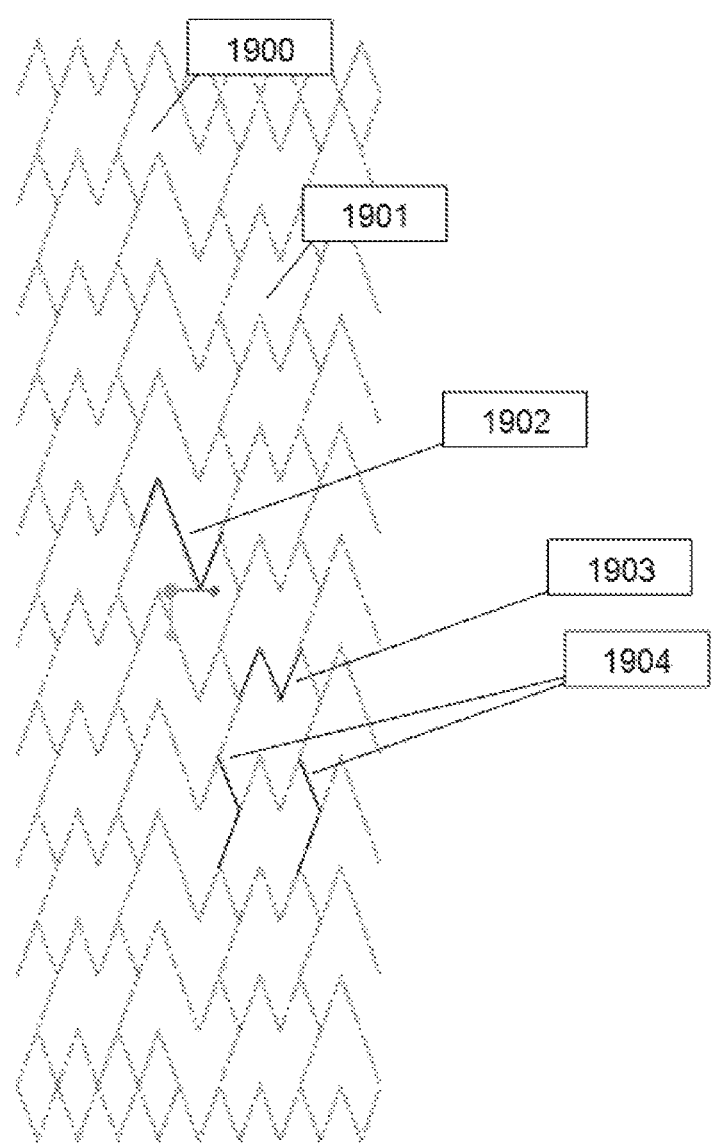
Figure 14C:
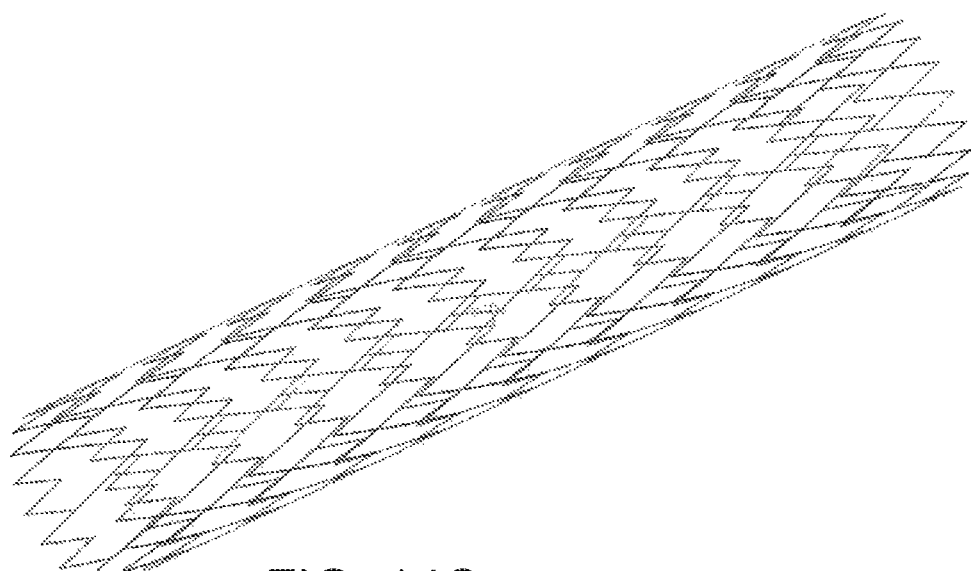

In some embodiments, vascular endoprostheses for the treatment of deep venous thrombosis, including in the iliac and common femoral veins, are provided, including vascular endoprostheses (e.g., stents) having high radial force and flexibility along their length. FIGS. 14A-14C illustrate various view of an embodiment of a stent (e.g., a circular stent) having both high radial force and flexibility along its length. FIG. 14A illustrates the stent from its front or top (i.e., perpendicular to the stent's longitudinal axis) while FIG. 14C illustrates the stent from a three-quarter's perspective or an isometric view. FIG. 14B illustrates the flat pattern of the stent. The pattern consists of large "Z" cell patterns 1900 and small "Z" cell patterns 1901. The staggered "Z" cell pattern allows for a high radial force along with maintained flexibility along the length of the stent. The "Z" patterns repeat along the length of the stent (e.g., vertical) but alternates in orientation along the diameter (e.g., horizontal) of the stent. The "Z" cell pattern is defined by large "Z" struts 1902, small "Z" struts 1903, and crossing link struts 1904.

Figure 15:
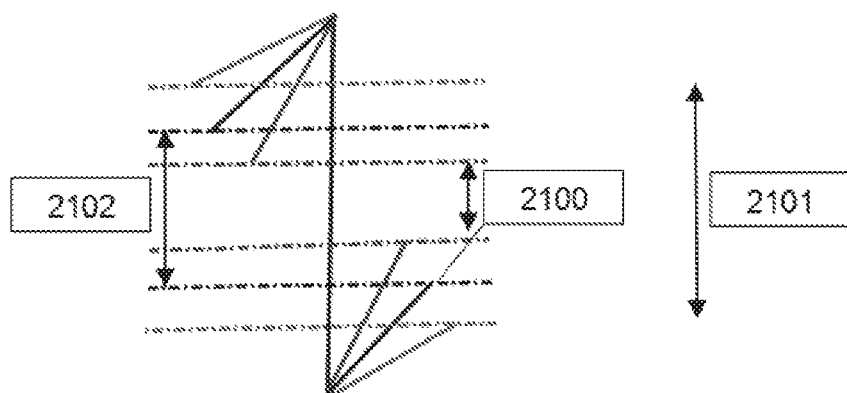
FIG. 15 shows a "Z" strut of the stent shown in FIGS. 14A-14C in various positions.

FIG. 15 illustrates a single "Z" strut of the stent shown in FIGS. 14A-14C in various positions. The middle "Z" strut is shown in the "Z" strut's relaxed or unconstrained position 2102. The most compressed "Z" strut is shown in the "Z" strut's compressed state 2100. And, the most spread out "Z" strut is shown in the "Z" strut's stretched state 2101. In some embodiments, the "Z" structure of the struts can advantageously allow each segment of the stent to independently articulate under loads, such as in bending. When the stent is bending, the top of the "Z" joint is in tension (e.g., absorbed by stretched state 2101) and the bottom of the arch is in compression (e.g., absorbed by compressed state 2011).

Currently available venous implants often lack the appropriate radial force necessary to resist compression and recoil of scarred, diseased veins while providing sufficient flexibility to account for the tortuosity and physiology of the peripheral venous system. In some embodiments, a venous implant for treating ilio-femoral venous outflow obstruction, vein compression, and venous insufficiency disease and methods for deploying such an implant are provided. The implant may provide a high radial force along with flexibility along its length and may be manufactured from self-expanding Nitinol. The implant may have sufficient radial force to resist compression/recoil of the diseased vein while providing flexibility and fatigue resistance. Additionally, the implant includes sufficient radial force to resist compression/recoil of scarred, diseased vein, while providing flexibility to resist kinking and good fatigue resistance. In some embodiments, the vascular implant is self-expanding.

Figure 16:
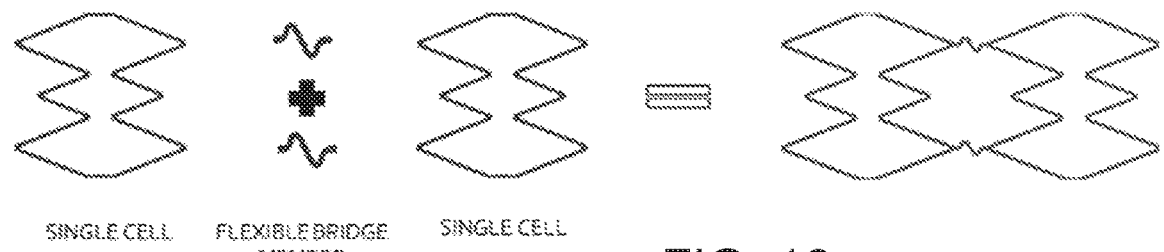
FIG. 16 shows the individual components, including cells and flexible bridge members of an embodiment of a stent.
Figure 17:
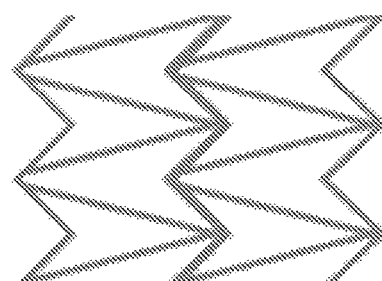
FIG. 17 shows a cell geometry having a high radial force.
Figure 18:
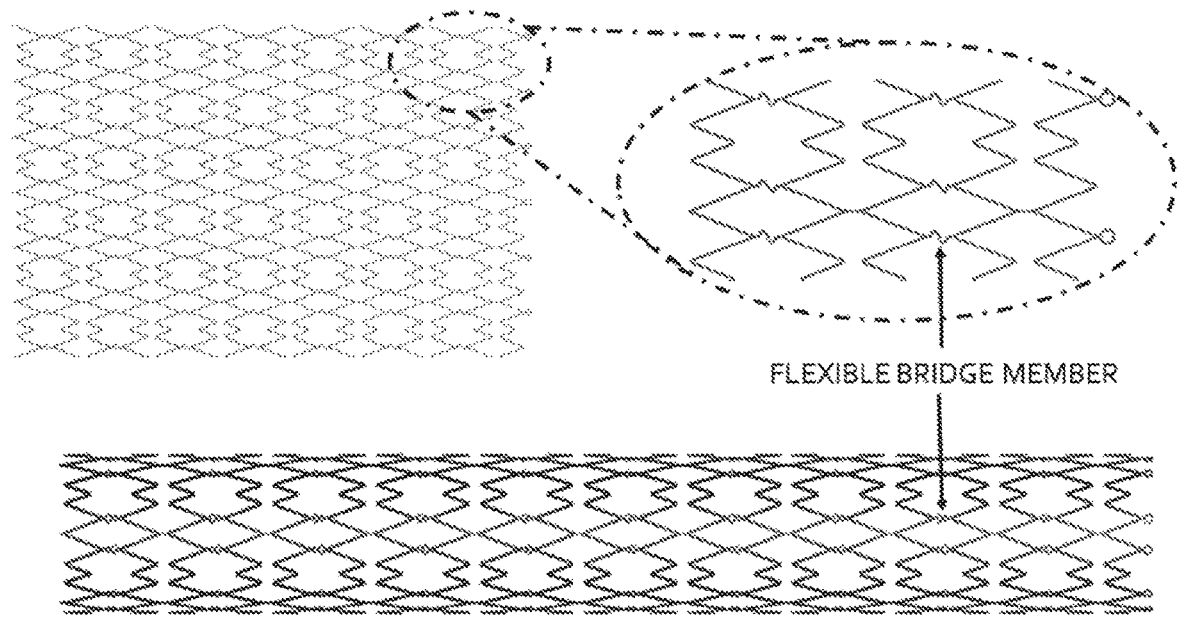
FIG. 18 illustrates a network of flexible constructs formed of cells and flexible bridge members.
Figure 19A:
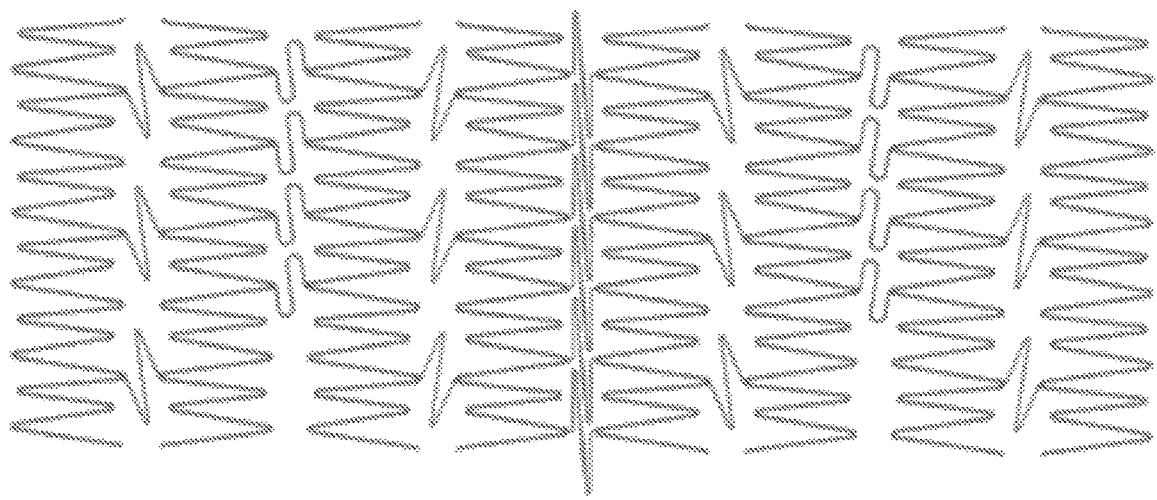
FIGS. 19A and 19B show various flexible bridge member geometries.
Figure 19B:
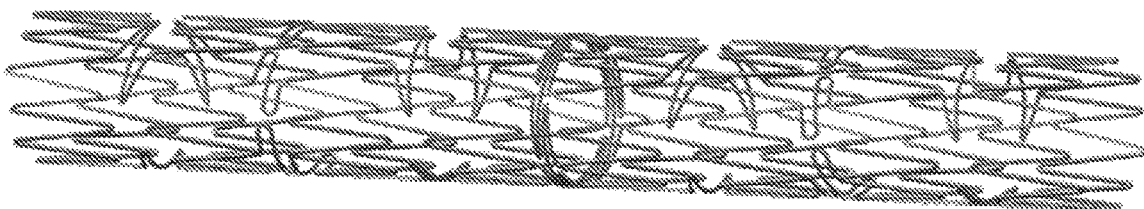

In some embodiments, an implant comprises a cylindrical, self-expanding stent (e.g., made of a shape-memory material, such as Nitinol) with individual circumferential stent frame/cell geometries joined by flexible bridge members. Repetition of such individual stent cells and flexible bridge members may make up the final diameter and total length of the stent. FIG. 16 illustrates an exemplary "equation" for the creation of such a stent. As can be seen on the left side of the "equation," a first single cell may be joined to a second single cell using two (or more) bridge members thereby forming a flexible construct. Multiple, if not many of these flexible constructs may be joined together to form a network. Alternatively, the flexible constructs may all be cut from a single tube. FIG. 18 illustrates a network of flexible constructs formed of cells and flexible bridge members. FIG. 17 illustrates a strut configuration that can give the resultant stent a high radial force. Flexible bridge members can be placed to join individual stent frame/cell geometries in alternate configurations resulting in different flexibility characteristics of the final stent. In some embodiments, the bridge members join the individual stent frame/cell geometry in a straight line continuous repeating pattern, as shown in FIG. 18. In other embodiments, the bridge members can be placed at varying intervals or in a helical or multi-helical configurations. FIGS. 19A and 19B illustrate additional flexible bridge member geometries—FIG. 19A is the same as FIG. 19B except that it is shown flat while FIG. 19B is shown as it would appear in a stent.

Figure 20G:
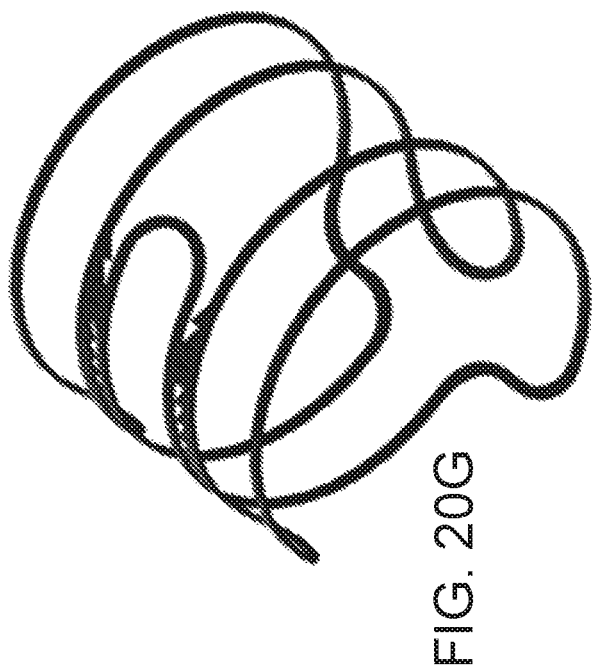
Figure 20H:
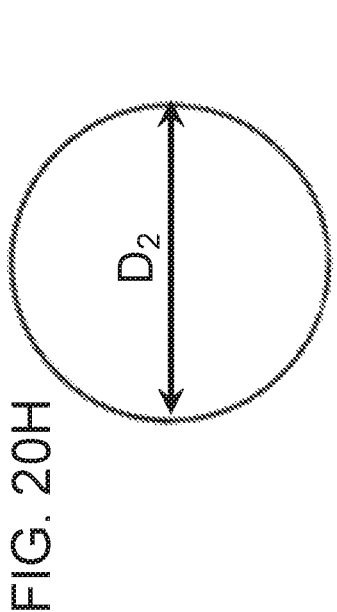
Figure 20E:
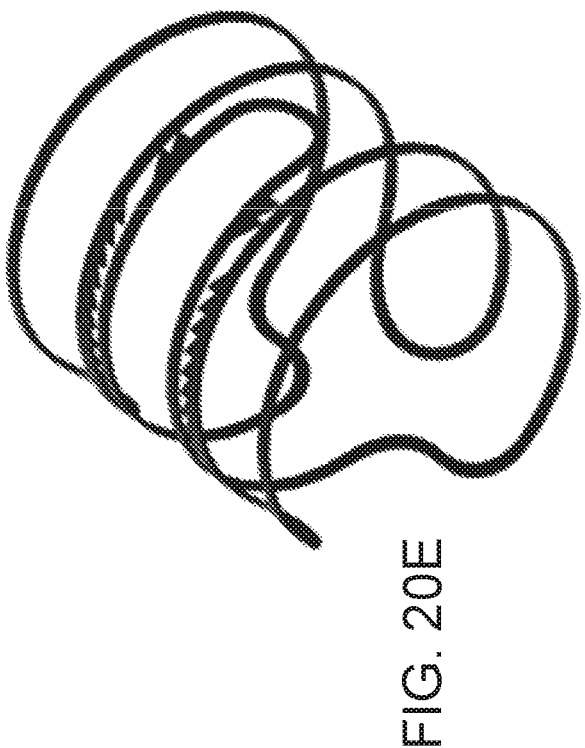
Figure 20F:
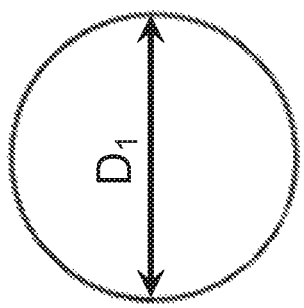

In some embodiments an implant is provided that has an expanded implantation size that may be selectively adjustable across a range of diameters. FIGS. 20A-20H illustrate various views of an implant manufactured from a super-elastic and/or shape memory tube (e.g., Nitinol) and laser cut with a series of engaging fingers or teeth. FIG. 20A illustrates the implant flat and laid out, with interlocking fingers at opposite ends of the implant. FIG. 20B illustrates a three-quarters view of the implant in its tubular conformation with at least some of the interlocking fingers being engaged. FIG. 20C illustrates a side view of the implant (perpendicular to the implant's longitudinal axis) showing a close-up of the interlocking fingers. FIG. 20D illustrates a front or top view of the implant. FIG. 20E illustrates the implant prior to expansion, finger interlocking, and deployment (in this figure no fingers are interlocked). FIG. 20F illustrates a top or front view of the implant showing the diameter prior to expansion/deployment (diameter D1). FIG. 20G illustrates the implant after expansion, finger interlocking, and deployment (in this figure at least some fingers are interlocked). FIG. 20H illustrates a top or front view of the implant showing the diameter after expansion/deployment (diameter D2). As can be seen, the diameter of the implant after deployment/expansion/interlocking of fingers (i.e., D2) is larger than the diameter of the implant before deployment/expansion/interlocking of fingers (i.e., D1).

To deploy the implant, the implant may be radially compressed/crimped to a smaller diameter for loading onto/into a delivery catheter. The implant may be crimped over a balloon on the inner core of the delivery system which may be later inflated to expand the coiled implant to the desired diameter. The engagement fingers are pre-configured at specific locations to allow discrete incremental expansion of the stent. In some embodiments, the implant can be expanded in 0.5 mm increments. In some embodiments more than one implant may be joined together. For example, the ultimate length of the implant can be controlled by joining any desired number of individual adaptive diameter cells via flexible or rigid bridge members.

Implants such as those described above may be advantageously provide an adaptive diameter and/or flexibility to conform the dynamic movement of peripheral veins in leg/pelvis thereby facilitating treatment of both iliac vein compression syndrome and ilio-femoral venous outflow obstructions.

It may be desirable to have a stent that will conform to the existing path of a vein instead of a straightening out of the vessel by the stent. It may also be desirable to have a high radial stiffness of the stent to resist collapse of the stent under crushing load and to maximize the resultant diameter of the treated vessel at the location of the stent deployment. With most stent constructions there is a direct relationship between radial stiffness and axial stiffness.

Common commercially available balloon expandable stents experience a dramatic change in length as a balloon is used to expand the stent within the vessel. Common commercially available self-expanding stents experience a change in length less dramatic, but still substantial, which increases with increasing stent length. Change in length between the configuration within the delivery system and when deployed in the vessel causes difficulty in placing/landing the stent precisely at the target location. When the stent is deployed in its crimped configuration and expanded, the shortening in length causes the stent target deployment location to have to offset from the target dwell location. The magnitude of this effect is not controllable or easily anticipated as it is dependent on the luminal cross-section along the length of the target dwell location (which is frequently and unexpectedly influenced by residual stenosis, irregular shape due to external objects, and/or forces, etc.). For target lesions leading up to the junction of the left and right iliac into the IVC, this causes difficulty in placing the stent to dwell completely within the iliac along its total length up to the junction to the inferior vena cava without crossing into the inferior vena cava.

In some embodiments a venous stent with high radial force, no impactful foreshortening along multiple lengths, and high flexibility/vessel conformity is provided. Minimization of foreshortening allows the stent advantageously accurate and predictable deployment. And, high flexibility maximizes the fatigue life of the stent under bending. Of course, it will be understood that the stent may find applications in the arterial system as well.

FIGS. 21A-21D illustrate various views of an embodiment of a stent configured to minimize foreshortening while retaining flexibility. The stent 100, which may be self-expanding, consists of a series of circumferentially adjacent closed cells 200 that define at least two axially repeating rings 301. Each axially repeating ring 301 has an inner diameter 101, an outer diameter 103, and a length 203. Each ring is connected by pairs of linkage struts 202 with the total length of the repeating rings 102 and linkage struts 202 defining the length of the stent. In some embodiments, the closed cells 200 may be defined by an enclosed perimeter.

The linkage struts 202 attach to the rings 301 at or near the attachment of each adjacent closed cell 202 in the ring 301. In this way, the linkage struts 202 are connected to portions of the rings 301 that never change axially upon compression or expansion of the ring—this advantageously improves the foreshortening properties of this stent. In some embodiments, the linkage struts 202 are configured in pairs to mirror each other on opposite sides of the stent 303 when the flat laser-cut pattern (shown in FIG. 21B) is cut into a tube as in FIGS. 21A & 21C. Is some embodiments, adjacent linkage struts 202 are positioned with at least one axially indexed cell rotation around the axis creating a spiral orientation of linkage struts 202 connecting the rings 301.

Figure 21A:
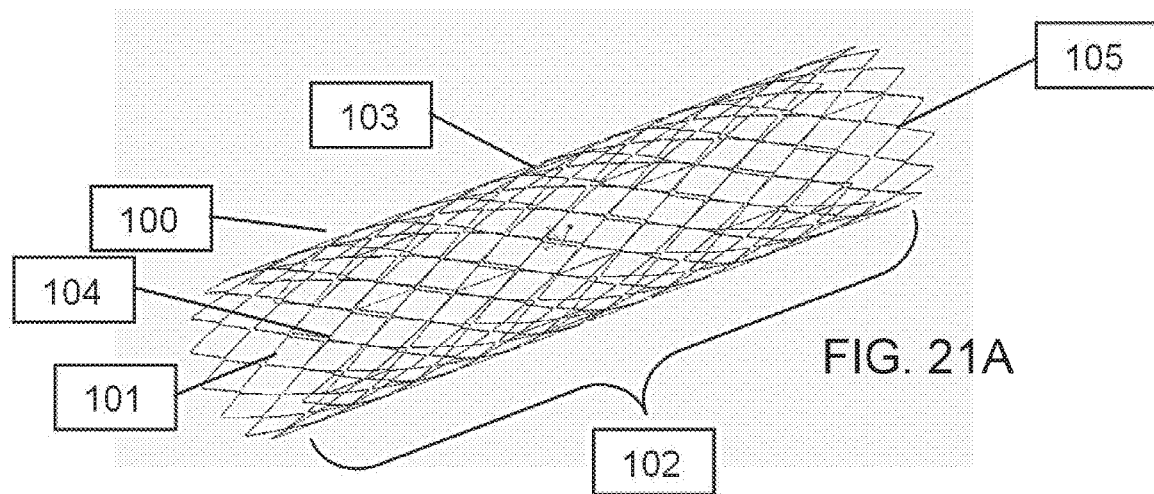
FIGS. 21A-21D show various views of an embodiment of a stent configured to minimize foreshortening while retaining flexibility.
Figure 21B:
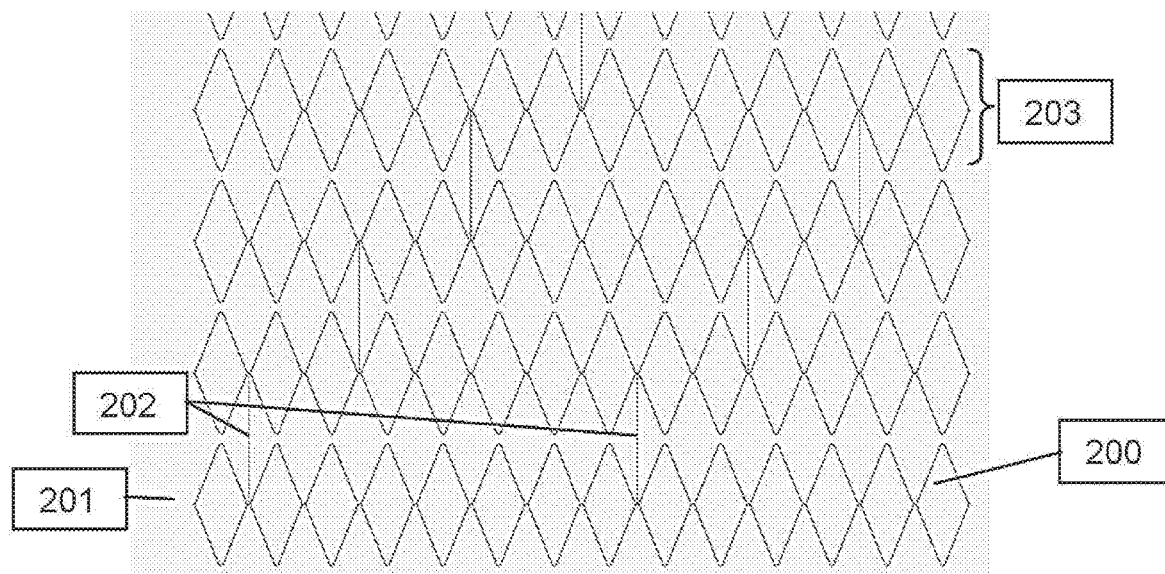
Figure 21C:
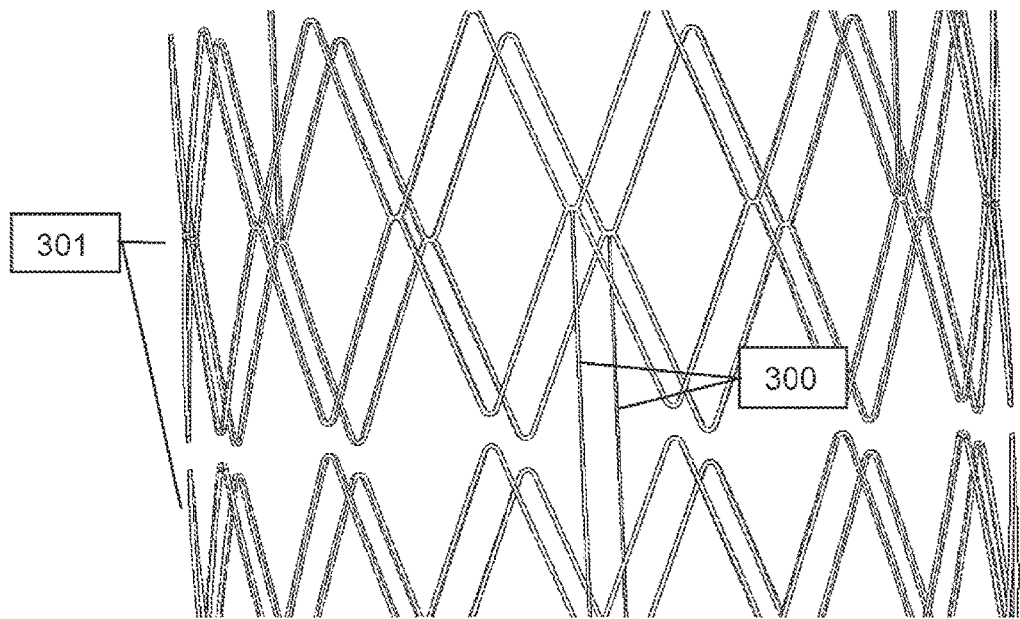
Figure 21D:
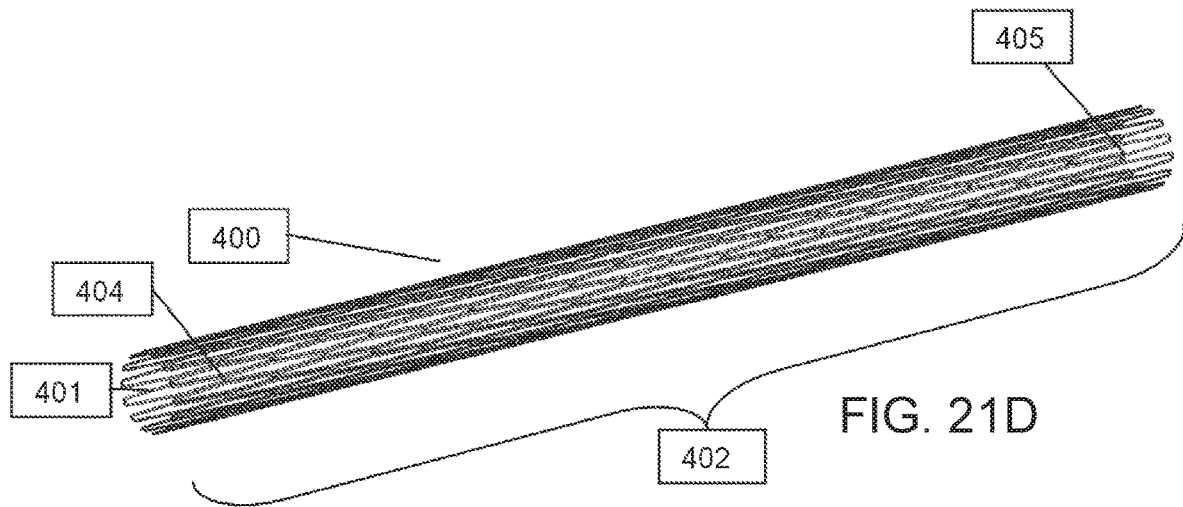

The stent has a first unconstrained/uncompressed configuration, shown in FIG. 21A, that is defined by a first diameter 101 and a first length 102. The stent also has a second crimped configuration, shown in FIG. 21D, that is defined by a second diameter 401 (that is less than the first diameter 101) and a second length 402. Because the linkage struts 202 are attached only at points on the rings 301 that do not move axially, the first length 102 and the second length 402 are substantially the same. There is only very little change in length only from the 1st half and trailing cell. In some embodiments, the length of the struts prevents contact of the cells in axially adjacent rings from making contact in the first unconstrained/uncompressed configuration and the second crimped configuration. In some embodiments, the spacing between the joining of the cells in the unconstrained state at the first end 104 and second end 105 substantially equals the spacing between the joining of the cells in the crimped state at the first end 404 and the second end 405. In some embodiments, there is a radiopaque marker at the joining location of the cells at the first end 104, 404 and second end 105, 405.

Some embodiments disclosed herein, such as those shown in FIGS. 21A-21D, decouple the relationship between radial stiffness and axial stiffness through their configuration of individual one cell long rings fixed together at the joining of the cells of each ring through the linkage struts. This allows for maintenance of controlled spacing by the linkage strut between the joined rings along a pathway but gives them the freedom to orient with the axis of one ring being different than the axis of the adjacent rings. The individual rings, with a relatively low axial flexibility, orient themselves largely straight along their individual length with the bending happening substantially along the linkage struts which are characterized by a much higher axial flexibility. Therefore, radial force can be controlled by the width of the cell struts and kept independent of the axial flexibility that is controlled by the width of the linkage struts. Additionally, the axially rotated indexing position of each adjacent pair of linkage struts, creating a spiral orientation of linkage struts, ensures that the stent has substantially similar axial flexibility regardless of angular orientation around its axis.

With each cell connected at the attachment of the struts, there is no change in position of one cell to the adjacent cells when the stent is fully crimped and when it's fully unconstrained. Therefore, the only foreshortening of the stent would come from half of the leading cell and half of the trailing cell. Also, the foreshortening of the presented invention is the same regardless of stent overall length given equally configured cells (increasing length by adding more rings). When the presented invention is deployed into the iliac-inferior vena cava (as discussed above), the location of the stent within the delivery system will equal the location of the stent when deployed form the delivery system into the vessel. The positioning and deployment of the stent will be the same regardless of the stent length. Therefore, a marker located at the connection of the cells/attachment of the struts can give excellent visualization and indication of the position of the stent when in the delivery system and when deployed in the vessel.

Currently available implants are typically loaded and retained onto a delivery system in a crimped configuration and then navigated and deployed in the desired anatomical location where they expand to the implanted configuration. The final implanted configuration can be achieved through mechanical expansion/actuation (e.g., balloon-expandable) or self-expansion (e.g., Nitinol). Self-expanding implants are manufactured from super elastic or shape memory alloy materials. Accurate and precise deployment of a self-expanding implant can be challenging due to a number of inherent design attributes associated with self-expanding implants. The implant may jump/advance from the distal end of the delivery system during deployment due to the stored elastic energy of the material. Additionally, the implant may foreshorten during deployment due to the change in the implant diameter from the crimped configuration to the expanded configuration. Finally, physiological and anatomical configurations, such a placement at or near bifurcations of body lumens, can affect accurate placement of implants.

Once the implant in placed within the body lumen there is potential for uneven expansion or lack of circumferential implant apposition to the body lumen which can result in movement, migration or in certain severe cases implant embolization.

In some embodiments, a self-expanding implant designed with sufficient radial force to resist constant compression of the body lumen while providing optimal fatigue resistance, accurate placement, and in-vivo anchoring to prevent is provided. Additionally, various methods for deployment and implantation for treating iliac vein compression syndrome and venous insufficiency disease are provided.

In some embodiments, the implant comprises a purposely designed venous implant intended to focally treat iliac vein compression (May-Thurner Syndrome). The implant may be relatively short in length (~40 mm) and may be manufactured from self-expending Nitinol with integrated anchor features to aid in accurate placement and to mitigate migration following implantation. The implant and delivery system are designed for precise deployment and placement at the bifurcation of the inferior vena cava into the right and left common iliac veins.

Figure 22A:
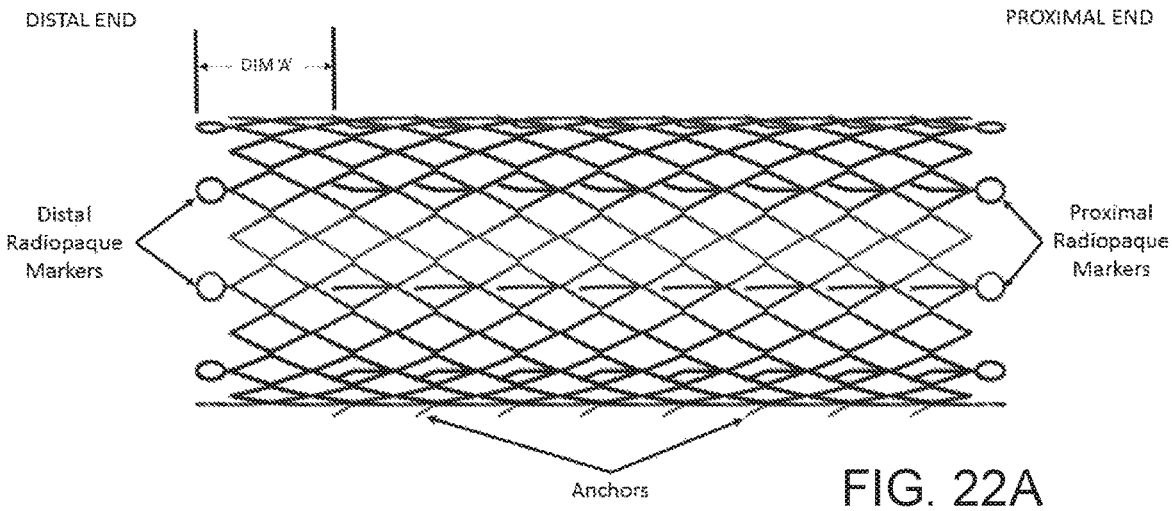
FIGS. 22A-22E show various views of an intravascular stent having a plurality of anchor members.
Figure 22B:
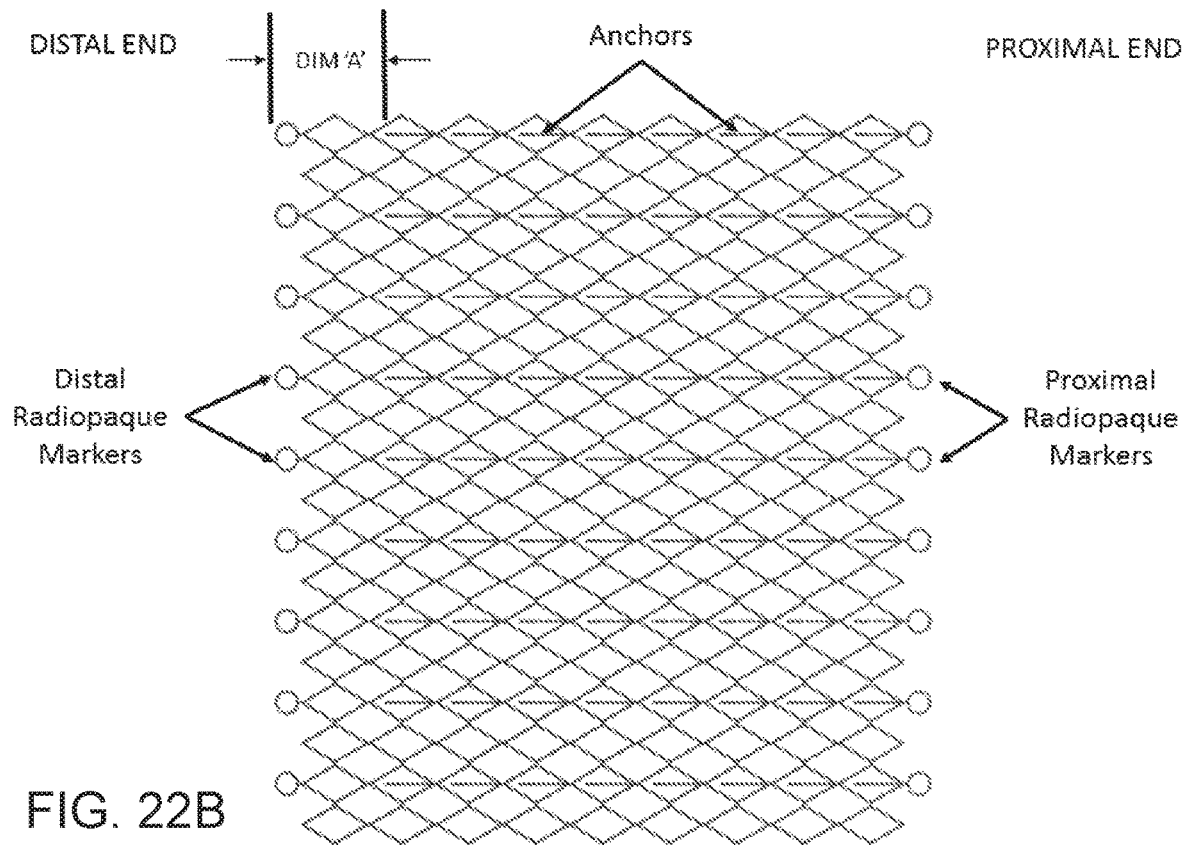
Figure 22C:
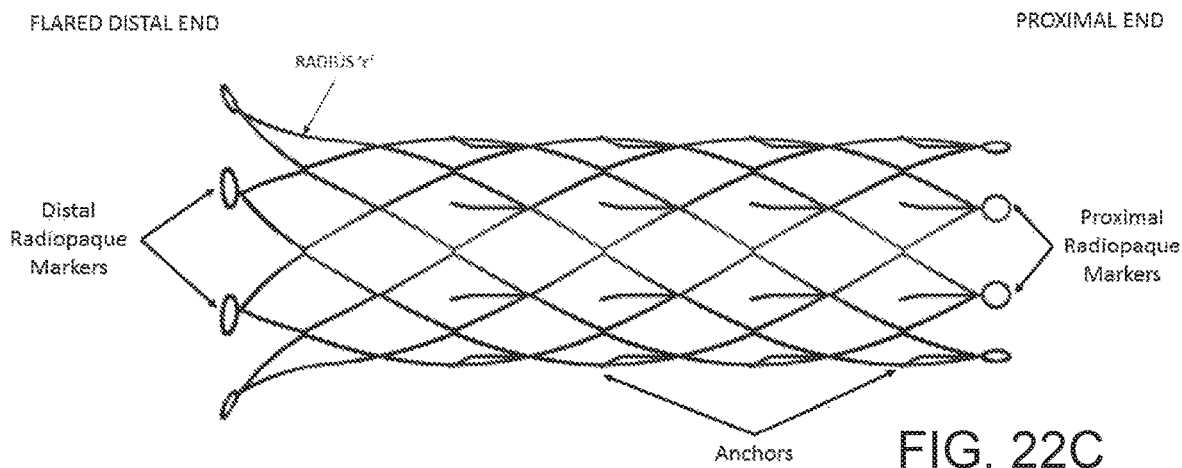
Figure 22D:
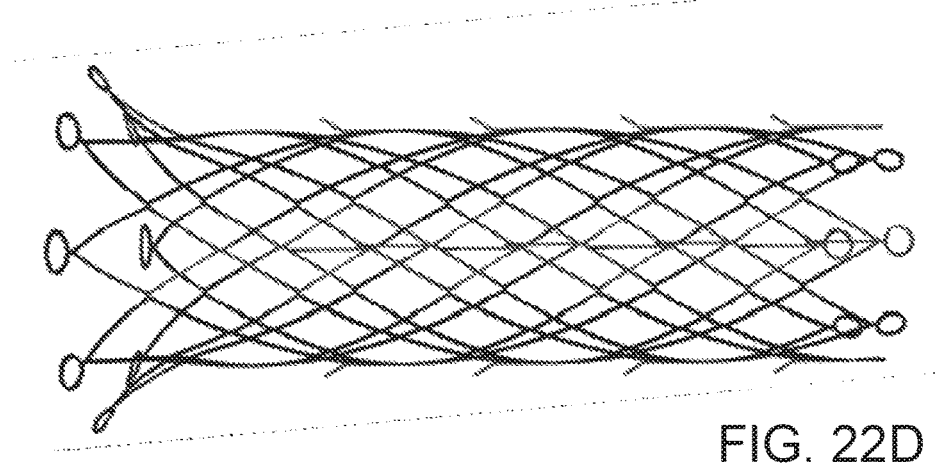
Figure 22E:
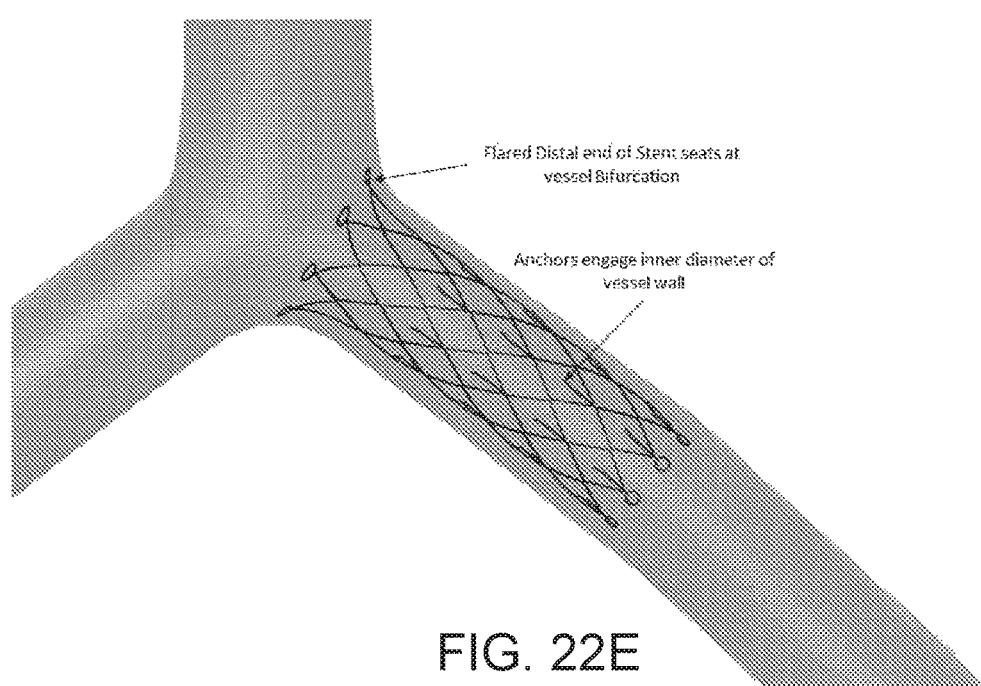
Figure 23A:
FIGS. 23A-23F show various potential configurations of anchors that may be used with the intravascular stent of FIGS. 22A-22E.
Figure 23D:
Figure 23B:
Figure 23E:
Figure 23C:
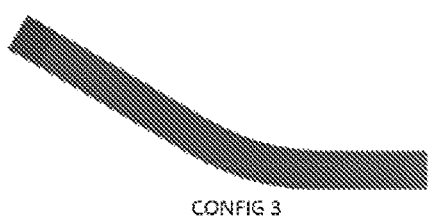
Figure 23F:

FIGS. 22A-22E illustrate various views of an intravascular stent having a plurality of anchor members. FIG. 22A illustrates the stent in a substantially cylindrical configuration. FIG. 22B illustrates the stent in a flat, laser cut pattern. FIGS. 22C and 22D illustrate the stent in a substantially uncompressed state. FIG. 22E illustrates the stent implanted within the left common iliac vein at the bifurcation of the inferior vena cava.

In one embodiment, the stent comprises a cylindrical self-expanding Nitinol structure with anchor features integrated into the stent frame cell pattern that are heat set into an angled configuration, thus resulting in anchor features circumferentially protruding outward from the base diameter of the stent when deployed. When the stent implant is crimped and loaded into a delivery catheter the anchors are constrained by the outer sheath of the delivery catheter thus allowing them to be flush with the base diameter of the stent.

As can be seen in FIG. 22B, the first set of anchor features may be set back a distance DIM 'A' from the distal end of the stent, thus allowing the stent to be partially deployed from the delivery system allowing the operator to finely reposition the entire delivery system as necessary such to align the distal end of the implant at the target deployment location. Once the distal end of the partially deployed stent is in the appropriate deployment location, the remainder of the stent can be deployed and the anchor features will engage the vessel wall upon deployment from the delivery catheter.

The anchor features may aid in accurate and precise deployment at the target implantation location of the stent. For example, engagement of the anchor features in the vessel wall may mitigate jumping of the implant from the delivery system and missing the target implantation location due to the expansion energy from self-expanding implants. Moreover, distal to proximal engagement of the anchor features in the vessel wall during deployment may serve to mitigate foreshortening of the implant in the distal-to-proximal direction. As the distal end of the implant is first anchored against the vessel wall the implant can only foreshorten in the proximal-to-distal direction during deployment as the distal end of the implant is fixed/anchored against the vessel wall. And, following implantation of the stent, the anchor features may help mitigate migration of the implant.

FIGS. 23A-23F show various potential configurations of anchors that may be used with the intravascular stent of FIGS. 22A-22E.

In another embodiment, shown clearly in FIGS. 22C and 22D, the implant with anchor features consists of a cylindrical self-expanding Nitinol stent with distal flared section. The distal flared section is controlled by radius 'r'. The flared distal end of the stent may be used for placement of the stent at a bifurcation of two vessels as shown in FIG. 22E.

The pre-loaded stent configuration on the delivery system allows the distal flared section of the stent to be partially deployed from the delivery system allowing the operator to position the flared section of the stent at the bifurcation of two vessels. The delivery catheter is advanced distal to the vessel bifurcation to be treated, in this case the left common iliac vein. Using the radiopaque markers on the implant, the operator can seat the partially deployed flare section of the stent at the bifurcation junction. Once the distal flared end of the partially deployed stent is in the appropriate deployment location and seated at the bifurcation junction the remainder of the stent can be deployed and the anchor features can engage the vessel wall upon deployment from the delivery catheter.

The implant shown in FIGS. 22A-23F may advantageously facilitate accurate and precise deployment of the stent implant, prevent migration of the stent implant following deployment, and mitigate protuberance of the stent implant into the inferior vena cava (causing hemodynamic insufficiencies) when treating iliac vein compression syndrome (May-Thurner syndrome).

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

Similarly, this method of disclosure, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

While various embodiments of the present invention have been described above, it should be understood that they have been presented by way of example only, and not limitation. It will be apparent to persons skilled in the relevant art that various changes in form and detail can be made therein without departing from the spirit and scope of the present invention. Thus, the breadth and scope of the present invention should not be limited by any of the above-described exemplary embodiments, but should be defined only in accordance with the following claims and their equivalents.

What is claimed is:

1. A self-expanding stent, comprising:
a plurality of rings adjacently positioned along a longitudinal axis of the stent, each of the rings including a plurality of struts interconnected to form alternating apexes and troughs; and
a plurality of flexible bridge members extending between adjacent pairs of the plurality of rings and connecting to at least one of the apexes to connect the adjacent pairs, wherein the flexible bridge members are formed in a plurality of different geometries and the geometry of the flexible bridge members varies from one pair of connected rings to the next adjacent pair of connected rings along the longitudinal axis of the stent, wherein the plurality of different geometries of flexible bridge members comprise generally s-shaped bridge members with two rounded bends, generally z-shaped bridge members with two acutely-angled bends, and nesting elongated generally z-shaped bridge members; wherein the generally s-shaped bridge members extending between adjacent pairs of the plurality of rings include a plurality of generally s-shaped bridge members extending between a first pair of rings of the plurality of rings, and wherein each of the plurality of generally s-shaped bridge members is connected to a pair of apexes aligned with one another in the direction of the longitudinal axis.

2. The stent of claim 1, wherein for each pair of connected rings, the flexible bridge members connect between at least one apex of one of the rings to at least one apex of another one of the rings.

3. The stent of claim 2, wherein for each pair of connected rings, the flexible bridge members connecting the pair of connected rings are spaced in a circumferential direction around the longitudinal axis such that each connected apex is separated from another connected apex by at least one unconnected apex.

4. The stent of claim 1, wherein for each pair of connected rings, the geometry of each of the flexible bridge members connecting the pair of connected rings is the same.

5. The stent of claim 1, wherein along the longitudinal axis of the stent:
a second pair of rings directly adjacent the first pair of rings are connected by the generally z-shaped bridge members;
a third pair of rings directly adjacent the first pair of rings are connected by the generally z-shaped bridge members; and
a fourth pair of rings directly adjacent the third pair of rings are connected by the nesting elongated z-shaped bridge members.

6. The stent of claim 1, wherein the flexible bridge members connecting at least one pair of connected rings comprise at least three bridge struts, the bridge struts neither parallel nor perpendicular to the longitudinal axis of the stent such that the flexible bridge members generally comprise two acute angles.

7. The stent of claim 6, wherein, along the longitudinal axis of the stent, the flexible bridge members connecting at least one pair of connected rings located to one side of a longitudinal midpoint of the stent comprise a bridge strut generally oriented in a first direction at an oblique angle relative to the longitudinal axis of the stent, and the flexible bridge members connecting at least one pair of connected rings located to another side of the longitudinal midpoint of the stent comprise a bridge strut generally oriented in a second direction opposite the first direction at an oblique angle relative to the longitudinal axis of the stent.

8. A self-expanding stent, comprising:
a plurality of rings adjacently positioned along a longitudinal axis of the stent, each of the rings including a plurality of struts interconnected to form alternating apexes and troughs; and
a plurality of flexible bridge members extending between apexes of adjacent pairs of the plurality of rings to connect the adjacent pairs, wherein the flexible bridge members are formed in a plurality of different geometries and the geometry of the flexible bridge members varies from one pair of connected rings to the next adjacent pair of connected rings along the longitudinal axis of the stent, wherein the plurality of different geometries of flexible bridge members comprise generally s-shaped bridge members with two rounded bends, generally z-shaped bridge members with two acutely-angled bends, and nesting elongated generally z-shaped bridge members, wherein the generally z-shaped bridge members extending between adjacent pairs of the plurality of rings include a plurality of generally z-shaped bridge members extending between a first pair of rings of the plurality of rings, and wherein each of the plurality of generally z-shaped bridge members is connected to a pair of apexes aligned with one another in the direction of the longitudinal axis.

9. The stent of claim 8, wherein along the longitudinal axis of the stent:
a second pair of rings directly adjacent the first pair of rings are connected by the generally s-shaped bridge members;
a third pair of rings directly adjacent the second pair of rings are connected by the generally z-shaped bridge members; and
a fourth pair of rings directly adjacent the third pair of rings are connected by the nesting elongated generally z-shaped bridge members.

10. The stent of claim 8, wherein for each pair of connected rings, the flexible bridge members connecting the pair of connected rings are spaced in a circumferential direction around the longitudinal axis such that each connected apex is separated from another connected apex by at least one unconnected apex.

11. The stent of claim 8, wherein for each pair of connected rings, the geometry of each of the flexible bridge members connecting the pair of connected rings is the same.

12. A self-expanding stent, comprising:
a plurality of rings adjacently positioned along a longitudinal axis of the stent, each of the rings including a plurality of struts interconnected to form alternating apexes and troughs; and
a plurality of flexible bridge members extending between apexes of adjacent pairs of the plurality of rings to connect the adjacent pairs,
wherein along the longitudinal axis of the stent:
a first pair of rings are connected by a first set of generally z-shaped bridge members, each of the generally z-shaped bridge members of the first set having two acutely-angled bends and a first angular orientation in a first direction and being connected to a pair of apexes aligned with one another in the direction of the longitudinal axis,
a second pair of rings directly adjacent the first pair of rings are connected by generally s-shaped bridge members, each of the generally s-shaped bridge members having two rounded bends and being connected to a pair of apexes aligned with one another in the direction of the longitudinal axis,
a third pair of rings directly adjacent the second pair of rings are connected by a second set of generally z-shaped bridge members, each of the generally z-shaped bridge members of the second set having two acutely-angled bends and a second angular orientation in a second direction that is generally opposite the first angular orientation and first direction, and
a fourth pair of rings directly adjacent the third pair of rings are connected by nesting elongated z-shaped bridge members.

13. The stent of claim 12, wherein for each pair of connected rings, the flexible bridge members connecting the pair of connected rings are spaced in a circumferential direction around the longitudinal axis such that each connected apex is separated from another connected apex by at least one unconnected apex.

14. The stent of claim 13, wherein along the longitudinal axis of the stent:
the generally z-shaped bridge members connecting the first pair of rings are spaced in the circumferential direction such that each connected apex is separated from another connected apex by three unconnected apexes;
the generally s-shaped bridge members connecting the second pair of rings are spaced in the circumferential direction such that each connected apex is separated from another connected apex by one unconnected apex;
the generally z-shaped bridge members connecting the third pair of rings are spaced in the circumferential direction such that each connected apex is separated from another connected apex by three unconnected apexes; and
the nesting elongated z-shaped bridge members connecting the fourth pair of rings are spaced in the circumferential direction such that each connected apex is separated from another connected apex by one unconnected apex.

15. The stent of claim 12, wherein for each pair of connected rings, the geometry of each of the flexible bridge members connecting the pair of rings is the same.

* * * * *